United States Patent [19]
Curiel et al.

[11] Patent Number: 6,028,059
[45] Date of Patent: *Feb. 22, 2000

[54] METHODS FOR MODULATING PROTEIN FUNCTION IN CELLS USING INTRACELLULAR ANTIBODY HOMOLOGUES

[75] Inventors: David T. Curiel; Jessy Deshane, both of Birmingham, Ala.

[73] Assignee: UAB Research Foundation, Birmingham, Ala.

[*] Notice: This patent is subject to a terminal disclaimer.

[21] Appl. No.: 08/668,706

[22] Filed: Jun. 24, 1996

Related U.S. Application Data

[63] Continuation-in-part of application No. 08/468,252, Jun. 6, 1995, which is a continuation of application No. 08/301,339, Sep. 6, 1994, abandoned.

[51] Int. Cl.⁷ .................................................... A61K 48/00
[52] U.S. Cl. .............................................................. 514/44
[58] Field of Search ............................ 435/172.3; 514/44

[56] References Cited

FOREIGN PATENT DOCUMENTS

WO 94/02610   2/1994   WIPO .

OTHER PUBLICATIONS

JG Altin et al (1991) Growth Factors 4: 145–155 (abstract only).
JR Starkey et al (1991) FASEB J 5: A1259.
JA Drebin et al (1986) Proc Natl Acad Sci USA 83: 9129–9133.
IM Harwerth et al (1993) Br J Cancer 68: 1140–1145.
J Deshane et al (1994) Gene Therapy 1: 332–337.
Werge et al FEBS 274 (1,2): 193, 1990.
Wels et al Cancer Res 52: 6310, 1992.
Wels et al J Steroid Biochem. Mol. Biol 43(1–3): 1, 1992.
Brocea et al BBRC 197(2): 422, 1993.
Marasco et al PNAS 90: 7889, 1993.
R. Hesketh (1995) The Oncogene Facts Book pp. 32–42.

*Primary Examiner*—Bruce R. Campell
*Attorney, Agent, or Firm*—Benjamin Aaron Adler

[57] ABSTRACT

Methods and compositions for modulating protein function in a cell involving intracellular expression of an antibody homologue that binds to the protein within the cell are disclosed. In a preferred embodiment, an antibody homologue, such as a single chain Fv (sFv) fragment, is expressed within an intracellular compartment of a cell, such as the endoplasmic reticulum (ER), to inhibit cell surface expression of a membrane protein. Preferably, the cell is a malignant mammalian cell and the protein is a cell surface receptor oncoprotein, such as erbB2. Intracellular binding of the antibody homologue to the receptor oncoprotein inhibits its surface expression and, moreover, inhibits cell proliferation and cell survival. Isolated nucleic acid molecules encoding anti-c-erbB2 antibody homologues, as well as recombinant expression ventors and host cells incorporating these nucleic acid molecules, are also disclosed.

9 Claims, 19 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE:
      (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:1:

AGGGTACCAT GGACGTCCAG CTGACC          26

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE:
      (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:2:

GCTCTAGATT AGGAGACGGT GACCGTGGTC C                                31

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE:
        (A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO:3:

Met Lys Ser His Ser Gln Val Phe Val Phe Leu Leu Leu Cys Val
               5                  10               15

Ser Gly Ala His Gly
          20

(2) INFORMATION FOR SEQ ID NO:4:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE:
        (A) DESCRIPTION: cDNA (iii) HYPOTHETICAL: No (iv) ANTI-SENSE: No (vi) ORIGINAL SOURCE:

(xi) SEQUENCE DESCRIPTION: SEQ ID NO:4:

ATG GAC CTG CAG CTG ACC CAG TCT CCA GCA ATC CTC TCT GCA TCT CCA        48
GGG GAG AAG GTC ACA ATG ACT TGC AGG GCC ACC CCA AGT GTA AGT TAC        96
ATG CAC TGG TAT CAG CAG AAG CCA GGA TCC TCC CCC AAA CCT TGG ATT       144
TAT ACC ACA TCC AAC CTG GCT TCT GGA GTC CCT GCT CGC TTC AGT GGC       192
GGT GGG TCT GGG ACC TCT TAC TCT CTC ACA GTC AGC AGA GTG GAG GCT       240
GAA GAT GCT GCC ACT TAT TAC TGC CAG CAG TGG AGT CGT AGC CCA CCC       288
ACG TTC GGA GGG GGG TCC AAG CTG GAA ATA AAA GGT TCT ACC TCT GGT       336
TCT GGT AAA TCT TCT GAA GGT AAA GGT GTG CAG CTG CAG GAG TCA GGA       384
CCT GAG GTG GTC AAG CCT GGA GGT TCA ATG AAG ATA TCC TGC AAG ACT       432
TCT GGT TAC TCA TTC ACT GGC CAC ACC ATG AAC TGG GTG AAG CAG AGC       480
CAT GGA AAG AAC CTT GAG TGG ATT GGA CTT ATT AAT CCT TAC AAT GGT       528
GAT ACT AAC TAC AAC CAG AAG TTC AAG GGC AAG GCC ACA TTT ACT GTA       576
GAC AAG TCG TCC AGC ACA GCC TAC ATG GAG CTC CTC AGT CTG ACA TCT       624
GAG GAC TCT GCA GTC TAT TAC TGT GCA AGG AGG GTT ACG GAC TGG TAC       672

```
TTC GAT GTC TGG GGG GCA GGG ACC ACG GTC ACC GTC TCC                711
```

(2) INFORMATION FOR SEQ ID NO:5:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE:
        (A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO:5:

```
Met Asp Leu Gln Leu Thr Gln Ser Pro Ala Ile Leu Ser Ala Ser Pro
                 5                  10                  15

Gly Gln Lys Val Thr Met Thr Cys Arg Ala Thr Pro Ser Leu Ser Tyr
             20                  25                  30

Met His Trp Tyr Gln Gln Lys Pro Gly Ser Ser Pro Lys Pro Trp Ile
         35                  40                  45

Tyr Thr Thr Ser Asn Leu Ala Ser Gly Val Pro Ala Arg Phe Ser Gly
 50                  55                  60

Gly Gly Ser Gly Thr Ser Tyr Ser Leu Thr Val Ser Arg Val Glu Ala
 65                  70                  75                  80

Glu Asp Ala Ala Thr Tyr Tyr Cys Gln Gln Trp Ser Arg Thr Pro Pro
                 85                  90                  95

Thr Phe Gly Gly Gly Ser Lys Leu Glu Ile Lys Arg Ser Thr Ser Gly
            100                 105                 110

Ser Gly Lys Ser Ser Glu Gly Lys Gly Val His Leu Gln Glu Ser Gly
        115                 120                 125

Pro Asp Val Val Lys Pro Gly Gly Ser Met Lys Ile Ser Cys Lys Thr
130                 135                 140

Ser Gly Tyr Ser Phe Thr Gly His Thr Met Asn Ser Val Lys Gln Thr
145                 150                 155                 160

His Gly Lys Asn Leu Glu Trp Ile Ala Leu Ile Asn Pro Tyr Asn Gly
                165                 170                 175

Asp Thr Asn Tyr Asn Gln Lys Phe Lys Gly Lys Ala Thr Phe Thr Val
            180                 185                 190

Asp Lys Ser Ser Ser Thr Ala Tyr Met Glu Leu Leu Ser Leu Thr Ser
        195                 200                 205

Glu Asp Ser Ala Val Tyr Tyr Cys Ala Arg Arg Val Thr Asp Trp Tyr
210                 215                 220

Phe Asp Val Trp Pro Ala Gly Thr Thr Val Thr Val Ser
225                 230                 235
```

METHODS FOR MODULATING PROTEIN FUNCTION IN CELLS USING INTRACELLULAR ANTIBODY HOMOLOGUES

REFERENCE TO RELATED APPLICATION

This is a continuation-in-part application of U.S. patent application Ser. No. 08/468,252, filed Jun. 6, 1995 which is a continuation of application Ser. No. 08/301,339, filed Sep. 6, 1994, now abandoned.

BACKGROUND OF THE INVENTION

Description of the Related Art

ErbB2 is a 185-kDa transmembrane protein kinase receptor with extensive homology to the family of epithelial growth factor receptors (Yarden Y., and Ullrich, A. (1988) *Ann. Rev. Biochem.* 57:443–478). Aberrant expression of the erbB2 gene may play an important role in neoplastic transformation and progression. In this regard, ectopic expression of erbB2 has been shown to be capable of transforming rodent fibroblasts in vitro (Hudziak, R., et al. (1987) *Proc. Natl. Acad. Sci. USA* 84:7159–7163). In addition, transgenic mice carrying either normal or mutant erbB2 develop a variety of tumors, predominantly including neoplasms of mammary origin (Muller, W. J., et al. (1988) *Cell* 54:105–115). Importantly, it has been shown that amplification and/or over-expression of the erbB2 gene occurs in a variety of human epithelial carcinomas, including malignancies of the breast, ovary, gastro-intestinal tract, salivary gland, and lung (Slamon, D. J. et al. (1989) *Science* 707–712; Semba, K., et al. (1985) *Proc. Natl. Acad. Sci. USA* 82:6497–6501; Fukushige, S. I., et al. (1986) *Mol. Cell Biol.* 6:955–958). In the instances of breast and ovarian carcinoma, a direct correlation has been noted between over-expression of erbB2 and aggressive tumor growth with reduced overal patient survival (Hynes, N. E. (1993) *Cancer Biology* 4:19–26; Gerdes, J., et al. (1984) *J. Immunol.* 133:1710–1715). There is a lack of effective therapy for erbB2 overexpressing tumors which, in many cases, do not respond well to chemotherapy.

The association of over-expression of the erbB2 gene product with poor clinical prognosis has led to the development of therapeutic strategies to target tumor cells exhibiting increased surface levels of erbB2. Towards this end, monoclonal antibodies (mAbs) have been developed which exhibit high affinity binding to the extracellular domains of the erbB2 protein (Fendly, B. M., et al. (1990) *Cancer Research* 50:1550–1558; Drebin, J. A., et al. (1988) *Oncogene* 2:387–394). A subset of these monoclonal antibodies can elicit growth inhibition of erbB2 over-expressing tumor cells both in vitro and in vivo (Drebin, J. A., et al. (1988) *Oncogene* 2:387–394). Clinical trials in humans have been undertaken which exploit the direct antiproliferative effect of anti-erbB2 monoclonal antibodies (Carter, P., et al. (1992) *Proc. Natl. Acad. Sci. USA* 89:4285–4289). The utility of antibody based tumor targeting has also been proposed in the context of radiolabeled anti-erbB2 monoclonal antibodies. In addition, antitumor therapies directed at erbB2 have been developed utilizing targeted immunotoxins. These experimental strategies have employed recombinant fusion proteins consisting of various bacterial toxins selectively targeted to tumor cells by virtue of single-chain anti-erbB2 antibody (sFv) moieties.

Alternative to the therapeutic strategies described above that target an antibody to erbB2 expressed on the surface of tumor cells, a number of anti-cancer gene therapy strategies have been developed which employ various methods of molecular ablation of inappropriately or overexpressed genes to revert the transformed phenotype. These strategies have included antisense nucleic acid-mediated inhibition directed at the transcriptional or translational level of gene expression in the context of dominant oncogenes and trans-dominant mutations to achieve functional inactivation of over-expressed growth factor receptors. Accordingly, given the overexpression of erbB2 in many forms of human cancers, manipulation of the expression and/or function of erbB2 in tumor cells may be beneficial therapeutically. In breast cancer, overexpression of the erbB-2 protein can result from gene amplification and/or transcription factor deregulation.

SUMMARY OF THE INVENTION

This invention pertains to methods and compositions for modulating protein function in a cell involving intracellular expression of an antibody homologue that binds to the protein within the cell, thereby altering the function of the protein. The invention is particularly applicable to inhibiting the surface expression of erbB2 on a malignant cell, to thereby inhibit proliferation and survival of the cell, although the methods of the invention can be similarly used to inhibit the function of other proteins. In contrast to other approaches for inhibiting erbB2 function which target cell-surface erbB2 (e.g., radiolabeled antibodies or immunotoxins) or the erbB2 gene or mRNA (e.g., antisense nucleic acid), the methods of the invention are based upon targeting of an immature intracellular form of erbB2. As demonstrated herein, disruption of surface expression of erbB2 by intracellular antibody ablation in malignant cells that overexpress erbB2 inhibits both cell proliferation and cell survival. Accordingly, the invention provides an alternative therapeutic approach for modulating oncoprotein function, and in particular erbB2 function.

To alter the function of erbB2 or other protein according to the invention, an antibody homologue specific for the protein is expressed intracellularly. To express an antibody homologue within a cell, a nucleic acid molecule encoding the antibody homologue, such as a recombinant expression vector encoding the antibody homologue, is introduced into the cell. Preferably, the antibody homologue used to modulate protein function is a single chain Fv (sFv) fragment, although whole antibodies, or antigen binding fragments thereof (e.g., Fab fragments may also be useful.

In a preferred embodiment of the invention, the antibody homologue is expressed within an intracellular compartment of a cell. In a particularly preferred embodiment, the antibody homologue is expressed in the endoplasmic reticulum (ER) to inhibit cell surface expression of a membrane protein (e.g., erbB2) as a result of binding of the antibody homologue to an immature form of the protein within the endoplasmic reticulum. Similarly, secretion of a soluble protein from a cell can be inhibited by expression of an antibody homologue within the endoplasmic reticulum of the cell. Targeting of an antibody homologue to an intracellular compartment such as the endoplasmic reticulum can be accomplished by incorporating an appropriate signal sequence into the antibody homologue.

In a particularly preferred embodiment of the invention, an antibody homologue is expressed intracellularly in a malignant mammalian cell to inhibit the function of an oncoprotein. Preferably, the oncoprotein is normally expressed on the cell surface and functions as a receptor (e.g., a receptor tyrosine kinase). A particularly preferred cell surface receptor oncoprotein to be inhibited is erbB2. Intracellular binding of the antibody homologue to the receptor oncoprotein inhibits its surface expression and, moreover, inhibits cell proliferation and cell survival. A nucleic acid molecule encoding an antibody homologue in a form that is expressed within the endoplasmic reticulum can be introduced into erbB2 overexpressing malignant cells, including epithelial carcinoma cells from such tissues and organs as breast, ovary, gastrointestinal tract, lung and salivary gland. A nucleic acid molecule encoding the antibody homologue can be introduced into malignant cells in vivo by, for example, use of a recombinant viral vector or other vector system suitable for delivery of genes to cells in vivo.

Another aspect of the invention pertains to an isolated nucleic acid molecule encoding an anti-erbB2 antibody homologue in a form that is expressed in a mammalian cell in an intracellular compartment, such as the endoplasmic reticulum. In one embodiment, the nucleic acid comprises a first nucleotide sequence encoding a signal sequence operatively linked in a 5' to 3' direction by a phosphodiester bond to a second nucleotide sequence encoding a single chain Fv fragment that binds a human erbB2 oncoprotein. The signal sequence encoded by the first nucleotide sequence directs expression of a protein which contains the signal sequence to an endoplasmic reticulum. The isolated nucleic acids of the invention can be incorporated into recombinant expression vectors, such as plasmid or viral vectors, to facilitate expression of the antibody homologue within a cell. Host cells, such as an epithelial carcinoma cell into which a recombinant expression vector of the invention has been introduced, are also described.

The present invention shows that intracellular expression of the anti-erbB-2 sFv induces targeted, tumor cell-specific cytotoxicity in a variety of human breast carcinoma cell lines is provided. Further, it is shown that the erbB-2 levels of the breast cancer target cells are predictive of tumor cell sensitivity to anti-erbB-2 sFv mediated cytotoxicity. The phenotypic effects resulting from intracellular expression of the anti-erbB-2 sFv on the human breast cancer cell lines MDA-MB-361, SK-BR-3, BT-474, MCF-7 and MDA-MB-231 were evaluated. Recombinant adenoviruses encoding either a reporter gene (AdCMVLacZ) or the endoplasmic reticulum (ER) directed anti-erbB-2 sFv (Ad21) were delivered to various breast cancer cell lines. Cell surface erbB-2 levels were determined by immunohistochemistry. Cell viability was determined by a proliferation assay and flourescent microscopy allowed visualization of apoptotic cells. An erbB-2 ELISA quantified the endogenous erbB-2 levels of each cell line.

The anti-erbB-2 sFv encoding adenovirus, Ad21, but not the β-galactosidase encoding adenovirus, AdCMVLacZ, down-regulated cell surface erbB-2 levels in the breast cancer cell lines. Ad21 was cytotoxic to >95% of the tumor cells in the MDA-MB-361 and SK-BR-3 lines, and >60% of the tumor cells in the BT-474 line. In marked contrast, the MCF-7 and MDA-MB-231 cell lines showed no change in the rate of cell proliferation following this treatment. The cytotoxic effects generated in the first three lines were a consequence of the induction of apoptosis by the anti-erbB-2 sFv. An ELISA specific for erbB-2 showed that the breast cancer cell lines most susceptible to the anti-erbB-2 sFv, MDA-MB-361, SK-BR-3, and BT-474, overexpressed the erbB-2 protein while the cell lines demonstrating no response to the anti-erbB-2 sFv, MCF-7 and MDA-MB-231, expressed the lowest levels of erbB-2. These results demonstrate that targeted killing of erbB-2 overexpressing cells via intracellular knockout can be accomplished in the context of breast carcinoma. Furthermore, erbB-2 levels in breast tumor cells may be predictive of their sensitivity to sFv-mediated killing.

Several human lung adenocarcinoma cell lines were stably and transiently transfected with the anti-erbB-2 sFv gene. The anti-erbB-2 sFv can cause specific cytotoxicity in lung cancer cells. A replication-deficient recombinant adenoviral vector expressing the anti-erbB-2 sFv construct was constructed. The anti-erbB-2 sFv encoding adenoviral vector produced high levels of cytotoxicity in lung cancer cells.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2A shows SKOV3 cells transfected with control plasmid pCDNA3. FIG. 2B shows SKOV3 cells transfected with pGT20 (non-endoplasmic reticulum form of anti-erbB2 sFv). FIG. 2C shows SKOV3 cells transfected with PGT21 (endoplasmic reticulum of anti-erbB2 sFv). Magnification is 400×.

FIG. 3A shows SKOV3 cells transfected with control plasmid pCDNA3. FIG. 3B shows SKOV3 cells transfected with pGT20 (non-endoplasmic reticulum form of anti-erbB2 sFv). FIG. 3C shows SKOV3 cells transfected with pGT21 (endoplasmic reticulum of anti-erbB2 sFv). Magnification is 400×.

DETAILED DESCRIPTION OF THE INVENTION

Figure 1:
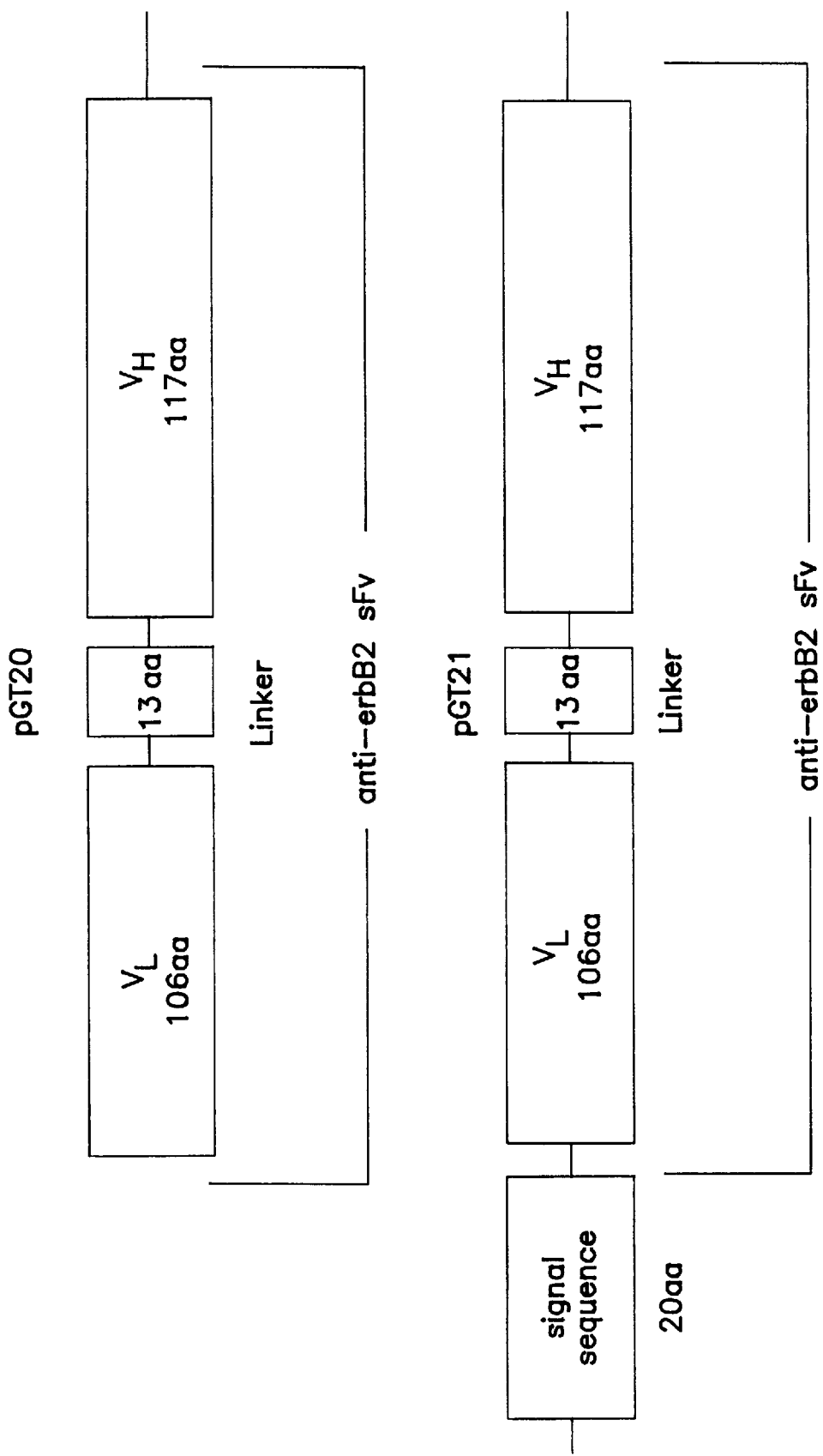
FIG. 1 is a schematic representation of the anti-erbB2 single chain antibody (sFv) gene constructs present in the pGT20 and pGT21 expression vectors.

This invention pertains to methods and compositions for modulating protein function in a cell involving intracellular expression of an antibody homologue that binds to the protein within the cell, thereby altering the function of the protein. The invention is described herein with regard in particular to inhibition of the expression of the erbB2 oncoprotein on the surface of erbB2 overexpressing tumor cells. However, the invention can be applied to modulating the function of other proteins as well.

Antibody Homologues

To inhibit the expression and/or function of a cellular protein according to the invention, as antibody homologue specific for the protein is expressed intracellularly such that the antibody homologue binds to the protein intracellularly, thereby inhibiting the protein's expression (e.g., on the cell surface) and/or function. A particularly preferred antibody homologue for use in the invention is a single chain Fv fragment (also referred to herein as a single chain antibody).

The term "antibody homologue" as used herein refers to whole immunoglobulin molecules, immunologically active portions or fragments thereof and recombinant forms of immunoglobulin molecules, or fragments thereof, that contain as antigen binding site which specifically binds an antigen e.g., a cellular protein. Additionally, the term antibody homologue is intended to encompass non-antibody molecules that mimic the antigen binding specificity of a particular antibody. Such agents are referred to herein as "antibody mimetic agents".

The term "antibody combining site", as used herein refers to that structural portion of an antibody molecule comprised of a heavy and light chain variable and hypervariable regions that specifically binds (immunoreacts with) antigen.

The terms "bind", "immunoreact" or "reactive with" in its various forms is used herein to refer to an interaction between an antigenic determinant-containing molecule and a molecule containing as antibody combining site, such as a whole antibody molecule or a portion therof, or recombinant antibody molecule (i.e., antibody homologue).

The term "monoclonal antibody" or "monoclonal antibody composition", as used herein, refers to a population of antibody molecules that contain only one species of an antigen binding site capable of immunoreacting with a particular epitope of an antigen. A monoclonal antibody composition thus typically displays a single binding affinity for a particular antigen with which it immunoreacts.

The term "immunogen" is used herein to describe a composition typically containing a peptide or protein as an active ingredient (i.e., antigen) used for the preparation of antibodies against the peptide or protein. Alternatively, the immunogen can be a nucleic acid (e.g., DNA) in a form suitable for expression of an encoded protein or peptide by cells upon introduction of the nucleic acid into the cells, with the expressed protein or peptide thereby acting as an antigen to stimulate an antibody response (so-called "intracellular immunization").

Structurally, the simplest naturally occurring antibody (e.g., IgG) comprises four polypeptide chains, two heavy (H) chains and two light (L) chains inter-connected by disulfide bonds. It has been shown that the antigen-binding function of an antibody can be performed by fragments of a naturally-occurring antibody. Thus, these antigen-binding fragments are intended to be encompassed by the term "antibody homologue". Examples of binding fragments include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment, which consists of a VH domain; (v) an isolated complimentarily determining region (CDR); and (vi) and F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single chain protein (referred to herein as single chain antibody or a single chain Fv (sFV); see e.g., Bird et al. (1988) Science 242:423–426; and Huston et al. (1988) Proc. Natl. Acad. Sci. USA 85:5879–5883). Such single chain antibodies are also encompassed within the term "antibody homologue". Other forms of recombinant antibodies, such as chimeric, humanized and bispecific antibodies are also within the scope of the invention.

Isolation of Antibody Genes

To express an antibody homologue within a cell, a nucleic acid molecule(s) encoding the antibody homologue is prepared and introduced into the cell. An isolated nucleic acid mulecule encoding an antibody homologue can be prepared according to standard molecular biology methods using nucleic acid sequences obtained from antibody genes. Isolated nucleic acid molecules encoding antibody chains (or relevant antigen binding portions thereof, such as VH and VL regions), specific for many different particular proteins have been described. Additionally, such nucleic acids can be isolated by standard techniques, for example, form a hybridoma that expresses a monoclonal antibody specific for a protein of interest or by screening an immunoglobulin expression library (e.g., an immunoglobulin phage display library) with a protein of interest.

Hybridomas

A hybridoma secreting a monoclonal antibody specific for a particular antigen is typically prepared by first immunizing a suitable subject with an appropriate immunogenic preparation of the antigen. The unit dose of immunogenic preparation and the immunication regimen will depend upon the species of mammal immunized, its immune status, the body weight of the mammal and the antigen concentration of the immunogenic preparation administered. For immunization, the immunogenic preparation is typically administered with an adjuvant, such as Freund's complete or incomplete adjuvant.

After a polyclonal antibody response against the antigen has been stimulated in the subject, antibody-producing cells (i.e., B lymphocytes) are recovered from the subject, fused with an immortalized cell line and the resultant hybridomas screened from production of a monoclonal antibody that binds the antigen (e.g., by an enzyme-linked immunosorbent assay (ELISA), radioimmunoassay, flow cytometry or other suitable assay). The technolocy for producing monoclonal antibody hybridomas is well known (see generally R. H. Kenneth, in *Monoclonal Antibodies: A New Dimension in Biological Analysis*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36).

Any suitable technique for preparing hybridomas can be used including, but are not limited to, the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Teh et al. (1976) *Proc. Natl. Acad. Sci. USA* 76:2927–31; and Yeh et al. (1982) *Int. J. Cancer* 29:269–75), and the more recent human B cell hybridoma technique (Kozbor et al. (1983) *Immunol. Today* 4:72), EBV-hybridoma technique (Cole et al. (1985), *Monoclonal Antibodies and Cancer Therapy*, Alan R. Liss, Inc., pp. 77–96) and trioma techniques. Moreover, the ordinary skilled worker will appreciate that there are many variations of such methods which also would be useful.

Typically, the immortal cell line (e.g., a myeloma cell line) is derived from the same mammalian species as the lymphocytes. For example, murine hybridomas can be made by fusing lymphocytes from a mouse immunized with an immunogenic preparation of a protein of interest with an immortalized mouse cell line. Preferred immortal cell lines are mouse myeloma cell lines that are sensitive to culture medium containing hypoxanthine, aminopterin and thymidine (HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed).

Once a hybridoma specific for a protein of interest is prepared, nucleic acid encoding the antibody chain (or relevant antigen binding portion thereof) expressed by the hybridoma can be isolated by standard techniques. For example cDNA can be prepared from mRNA obtained from the hybridoma and DNA encoding the antibody chain, or portion thereof, can be amplified by the polymerase chain reaction (PCR) to isolate DNA encoding an antibody chain. Alternatively, the cDNA (e.g., in a cDNA library) can be screened with an appropriate probe specific for antibody genes to isolate DNA encoding an antibody chain. The nucleic acid so isolated can be further manipulated (e.g., linked to other nucleic acid sequences) and subcloned into expression vectors using standard recombinant DNA techniques.

Recombinant Immunoglobulin Libraries

Alternatively, monoclonal antibodies can be prepared by constructing a recombinant immunoglobulin library, such as a sFv or Fab phage display library and nucleic acid encoding an antibody chain (or portion thereof) can be isolated therefrom. Immunoglobulin light chain and heavy chain first strand cDNAs can be prepared from mRNA derived from lymphocytes of a subject immunized with a protein of interest using primers specific for a constant region of the heavy chain and the constant region of each of the κ and γ light chains. Using primers specific for the variable and constant regions, the heavy and light chain cDNAs can then be amplified by PCR. The amplified DNA is then ligated into appropriate vectors for further manipulation in generating a library of display packages. Restriction endonuclease recognition sequences may also be incorporated into the primers to allow for the cloning of the amplified fragment into a vector in a predetermined reading frame for expression on the surface of the display package.

The immunoglobulin library is expressed by a population of display packages, preferably derived from filamentous phage, to form an antibody display library. In addition to commercially available kits for generating phage display libraries (e.g., the Pharmacia Recombinant Phage Antibody System, Catalog No. 240612), examples of methods and reagents particularly amenable for use in generating antibody display library can be found in, for example, Ladner et al. U.S. Pat. No. 5,223,409; Kang et al. International Publication No. WO 92/18619; Dower et al. International Publication No. WO 91/17271; Winter et al. International Publication No. WO 92/20791; Markland et al. International Publication No. 92/15679; Breitling et al. International Publication No. WO 93/01288; McCafferty et al. International Publication No. WO 92/01047; Garrard et al. International Publication no. WO 92/09690; Ladner et al. International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; and Barbas et al. (1991) *Proc. Natl. Acad. Sci. USA* 88:7978–7982. As generally described in McCafferty et al. *Nature* (1990) 348:552–554, complete VH and VL domains of an antibody, joined by a flexible $(Gly_4-Ser)_3$ linker, can be used to produce a single chain antibody expressed on the surface of a display package, such as a filamentous phage.

Once displayed on the surface of a display package (e.g., filamentous phage), the antibody library is screened with a protein of interest to identify and isolate packages that express an antibody that binds the protein of interest. Display packages expressing antibodies that bind immobilized protein can then be selected. Following screening and identification of a monoclonal antibody (e.g., a monoclonal sFv) specific for the protein of interest, nucleic acid encoding the selected antibody can be recovered from the display package (e.g., from the phage genome) by standard techniques. The nucleic acid so isolated can be further manipulated if desired (e.g., linked to other nucleic acid sequences) and subcloned into other expression vecotes by standard recombinant DNA techniques.

Manipulation of Antibody Genes

Once isolated, nucleic acid molecules encoding antibody chains, or portions thereof, can be further manipulated using standard recombinant DNA techniques. For example, a single chain antibody gene can be created by linking a VL coding region to a VH coding region via a nucleotide sequence encoding a flexible linker (e.g., $(Gly_4-Ser)_3$). Single chain antibodies can be engineered in accordance with the teachings of Bird et al. (1988) *Science* 242:423–426; Huston et al. (1988) *Proc. Natl. Acad. Sci. USA* 85:5879–5883; Ladner et al. International Publication No. WO 88/06630; and McCafferty et al. International Publication No. WO 92/10147. A preferred single chain antibody for use in the invention binds to the human erbB2 oncoprotein (referred to herein as an anti-erbB2 sFv). A plasmid (e23scFv) encoding an anti-erbB2 sFv immunotoxin is described in Batra, J. K. et al. (1992) *Proc. Natl. Acad. Sci. USA* 89:5867–5871. The anti-erbB2 sFv portion of this construct can be obtained by PCR using the e23scFv plasmid as the template and oligonucleotide primers shown in SEQ ID NO:1 and 2, as described in Example 1. The nucleotide and amino acid sequences of the anti-erbB2 sFv is shown in SEQ ID NO: 4 and 5, respectively. The anti-erbB2 sFv coding region can be linked to other sequences, e.g., sequences that direct expression of the sFv to a particular cellular location.

Another manipulation that can be performed on isolated antibody genes is to link the antibody gene to a nucleotide sequence encoding an amino acid sequence that directs the antibody homologue to a particular intracellular compartment. A preferred nucleotide sequence to which an antibody gene is linked encodes a signal sequence (also referred to as a leader peptide). Signal sequences are art-recognized amino acid sequences that direct a protein containing the signal sequence at its amino-terminal end to the endoplasmic reticulum (ER). Typically, signal sequences comprise a number hydrophobic amino acid residues. An example of a suitable signal sequence which can be linked to an antibody homologue to direct it to the endoplasmic reticulum is shown in SEQ ID NO: 3, although other suitable signal sequences can also be used. A nucleotide sequence encoding a signal sequence can be linked to an antibody gene by standard PCR techniques.

Alternatively, an antibody homologue can be linked to an amino acid sequence that directs the antibody homologue to a different compartment of the cell. For example, a nuclear localization sequence (NLS) can be linked to the antibody homologue to direct the antibody homologue to the cell nucleus. Nuclear localization sequences are art-recognized targeting sequences. Typically, a nuclear localization sequence is composed of a number of basic amino acid residues.

Yet another possible manipulation of antibody genes is to engineer chimeric and humanized antibody derivatives. Chimeric and humanized antibodies, which combine regions of animal and human antibodies, retain the antigenic binding specificity of the original monoclonal antibody, but may be less immunogenic than entirely animal-derived antibodies when used in humans. The terms "chimeric antibody" as used herein refers to an antibody molecules that combines a non-human animal variable region and a human constant region. To create a chimeric antibody gene, a gene encoding the constant region of a non-human antibody molecule is substituted with a gene encoding a human constant region. (see Robinson et al. International Patent Application No. PCT/US86/02269; Akira et al. European Patent Application No. 173,494; Neuberger et al. International Publication No. WO86/01533; Cabilly et al. U.S. Pat. No. 4,816,567; Cabilly et al. European Patent Application No. 125,023; Better et al. (1988) *Science* 240:1041–1043); Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl.*

Cancer Inst. 80:1553–1559). A chimeric antibody can be further "humanized" by replacing portions of the animal variable region not involved in antigen binding with equivalent portions from human variable regions. General reviews of "humanized" chimeric antibodies are provided by Morrison, S. L. (1985) Science 229:1202–1207 and by Oi et al. (1986) BioTechniques 4:214. Suitable "humanized antibodies can be produced by CDR or CEA substitution (see U.S. Pat. No. 5,225,539; Jones et al. (1986) Nature 321:552–525; Verhoeyan et al. (1988) Science 239:1534; and Beidler et al. (1988) J. Immunol. 141:4053–4060).

Antibody Mimetic Agents

In another embodiment, an antibody homologue of the invention is a non-antibody molecule that binds a protein of interest, thereby mimicking the binding ability of an antibody specific for the protein of interest. These agents are referred to herein as "antibody mimetic agents". An antibody mimetic agent may be a peptide that binds specifically to a protein or may be a natural ligand for a protein of interest (e.g., a ligand for a surface receptor). Additionally, the antibody mimetic agent may be only a portion of a natural ligand for the protein of interest, wherein the ligand portion retains the ability to bind to the protein of interest.

To isolate a nucleic acid molecule encoding a peptidic antibody mimetic agent that binds a protein of interest, a library of peptides (e.g., 5–20 amino acids in length) can be synthesized and screened for the ability to bind the immobilized protein. For general descriptions of peptide library construction and screening see U.S. Pat. No. 4,833,092; Scott, J. and Smith, G. P. (1990) Science 249:86–90; Devlin, J. et al. (1990) Science 249:404–407. Nucleic acid encoding the peptide can then be recovered from the library or the peptide can be sequenced by standard techniques and a nucleotide sequence encoding the peptide than deduced from the amino acid sequence of the peptide.

Expression of Antibody Homologues in Cells

An antibody homologue is expressed intracellularly in a host cell by introducing a recombinant expression vector containing nucleotide sequences encoding the antibody homologue into a host cell. Following isolation of antibody genes further manipulation of the sequences, DNA encoding the antibody homologue can be inserted into an expression vector to facilitate transcription and translation of the antibody coding sequences in a host cell. Within the expression vector, the sequences encoding the antibody homologue are operatively linked to transcriptional and translational control sequences. These control sequences include promoters, enhancers and other expression control elements (e.g., poly-adenylation signals). Such regulatory sequences are known to those skilled in the art and are described in Goeddel, *Gene Expression Technology: Methods in Enzymology* 185, Academic Press, San Diego, Calif. (1990). The expression vector and expression control sequences are chosen to be compatible with the host cell used. Expression vectors can be used to express one antibody chain (e.g., a single chain antibody) or two antibody chains (e.g., a Fab fragment). To express two antibody chains, typically the genes for both chains are inserted into the same expression vector but linked to separate control elements.

Expression of a nucleic acid in mammalian cells is accomplished using a mammalian expression vector. When used in mammalian cells, the expression vector's control functions are often provided by viral material. For example, commonly used promoters are derived from polyoma, Adenovirus 2, cytomegalovirus (CMV) and Simian Virus 40. An example of a suitable mammalian expression vector is pCDNA3 (commercially available from Invitrogen), which drives transcription via the CMV early intermediate promoter/enhancer and contains a neomycin resistance gene as a selective marker. Other examples of mammalian expression vectors include pCDM8 (Seed, B., (1987) *Nature* 329:840) and pMT2PC (Kaufman et al. (1987) *EMBO J.* 6:187–195). Alternative to the use of constitutively active viral regulatory sequences, expression of an antibody homologue gene can be controlled by a tissue-specific regulatory element that directs expression of the nucleic acid preferentially in a particular cell type. Tissue-specific regulatory elements are known in the art.

In one embodiment, a recombinant expression vector of the invention is a plasmid vector. Plasmid DNA can be introduced into cells by a variety of techniques, either as naked DNA or, more commonly, as DNA complexed with or combined with another substance. Alternatively, in another embodiment, the recombinant expression vector of the invention is a virus, or portion thereof, which allows for expression of a nucleic acid introduced into the viral nucleic acid. For example, replication defective retroviruses, adenoviruses and adeno-associated viruses can be used for recombinant expression of antibody homologue genes. Viral mediated gene transfer into cells can be accomplished by infecting the target cell with the viral vector.

Methods for introducing nucleic acid into cells have been described in the art. Many of these methods can be applied to cells either in vitro or in vivo. Non-limiting examples of techniques which can be used to intoduce an expression vector encoding an antibody homologue into a host cell include:

Adenovirus-Polylysine DNA Complexes: Naked DNA can be introduced into cells by complexing the DNA to a cation, such as polylysine, which is then coupled to the exterior of an adenovirus virion, e.g., through an antibody bridge, wherein the antibody is specific for the adenovirus molecule and the polylysine is covalently coupled to the antibody. see Curiel, D. T., et al. (1992) *Human Gene Therapy* 3:147–154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Receptor-Mediated DNA Uptake: Naked DNA can also be introduced into cells by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. Receptors to which a DNA-ligand complex have targeted include the transferrin receptor and the asialoglycoprotein receptor. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al (1991) *Proc. Natl. Acad. Sci. USA* 88:8850; and Cotten, M. et al. (1992) *Proc. Natl. Acad. Sci. USA* 89:6094–6098; Wagner, E. et al. (1992) *Proc. Natl. Acad. Sci. USA* 89:6099–6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Liposome-Mediated transfection ("lipofection"): Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in *Current Protocols in Colecular Biology*, Ausubel, F. M. et al. (eds.) Green Publishing Associates, (1989), Section 9.4 and other standard laboratory manuals. Additionally, gene delivery in vivo has been accomplished using liposomes. Nicolau et al. (1987) *Meth. Enz.* 149:157–176; Wang and Huang (1987) *Proc. Natl. Acad. Sci. USA* 84:7851–7855; Brigham et al. (1989) *Am. J. Med. Sci.* 298:278; and Gould-Fogerite et al. (1989) *Gene* 84:429–438.

Direct Injection: Naked DNA can be introduced into cells by directly injecting the DNA into the cells. For an in vitro culture of cells, DNA can be introduced by microinjection, although this is not practical for large numbers of cells. Direct injection has also been used to introduce naked DNA into cells in vivo (see e.g., Acsadi et al. (1991) *Nature* 332:815–818; Wolff et al. (1990) *Science* 247:1465– 1468). A delivery apparatus (e.g., a "gene gun") for injecting DNA into cells in vivo can be used. Such an apparatus is commercially available (e.g., from BioRad).

Retroviral Mediated Gene Transfer: Defective retroviruses were characterized for use in gene transfer for gene therapy purposes (Miller, A. D. (1990) *Blood* 76:271). A recombinant retrovirus can be constructed having a nucleic acid encoding a gene of interest (e.g., an antibody homologue) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:541–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application No. WO 89/07136; PCT Application No. WO 89/02468; PCT Application No. WO 89/05345; and PCT Application No. WO 92/07573.

Adenoviral Mediated Gene Transfer: The genome of an adenovirus can be manipulated such that it encodes and expresses a gene product of interest (e.g., an antibody homologue) but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenviral genome for foreign DNA is large (up to 8 kilobases) relative to many other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viral Mediated Gene Transfer: Adeno-associated virus (AAV) is a naturally occurring defective virus that requres another virus, such as an adenovirus or a herpes virus, as a helper virus for efficient replication and a productive life cycle. (Muzyczka et al. *Curr. Topics in Micro. and Immunol.* (1992) 158:97–129). It is also one of the few viruses that may integrate its DNA into non-dividing cells, and exhibits a high frequency of stable integration (Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected by Northern blotting, RNase protection or reverse transcriptase-polymerase chain reaction (RT-PCR). Expression of the introduced gene product (e.g., the antibody homologue) in the cell can be detected by an appropriate assay for detecting proteins, for example, by immunohistochemistry.

As will be appreciated by those skilled in the art, the choice of expression vector system will depend, at least in part, on the host cell targeted for introduction of the nucleic acid. For example, nucleic acid encoding an anti-erbB2 antibody homologue (e.g., anti-erbB2 sFv) is preferably introduced into erbB2 overexpressing tumor cells. Tumor cells known to overexpress erbB2 include epithelial carcinoma cells, such as carcinoma cells derived from tissues or organs including breast, ovary, lung, gastrointestinal tract and salivary gland. Preferred expression vectors and delivery systems for introducing nucleic acid into epithelial carcinoma cells include transfection with adenoviral-polylysine DNA complexes (see Example 2) and adenoviral vector-mediated gene transfer. These delivery systems are suitable for introduction of nucleic acid into cells in vitro, or more preferably for tumor cells, in vivo.

Modulation of Protein Function by Intracellular Antibody Homologue Expression

As described herein, the function of a protein can be modulated by expression intracellularly of an antibody homologue that binds to the protein. In a preferred embodiment of the invention, proliferation of a cell expressing a protein that stimulates expression of the cell is inhibited by introducing into the cell a nucleic acid molecule encoding an antibody homologue that binds to the protein intracellularly. Preferably, the protein that stimulates proliferation of a cell is an oncoprotein and the cell is a malignant mammalian cell. The term "oncoprotein" is intended to refer to the gene product of an oncogene. A "malignant cell" is intended to refer to a transformed, tumorigenic cell. A particularly preferred oncoprotein to be inhibited is erbB2. The term "erbB2" as used herein is intended to refer to the erbB2 oncoprotein in its various form, including the juman c-erbB2 oncoprotein (also referred to as the HER2 gene product), murine c-erbB2 (also referred to as the neu gene product) and the chicken v-erbB2 gene product.

In another preferred embodiment, cell surface expression of a protein normally expressed on the surface of a cell is inhibited by introducing into the cell a nucleic acid molecule encoding an antibody homologue that binds to the protein within an intracellular compartment (e.g., the endoplasmic reticulum). A particularly preferred cell surface protein to be inhibited is erbB2.

In yet another embodiment, the invention provides a method for inhibiting proliferation or survival of erbB2-overexpressing tumor cells in a mammal. The method involves introducing into the tumor cells a nucleic acid molecule encoding an antibody homologue, wherein the antibody homologue is expressed intracellularly and binds to erbB2 intracellularly within an intracellular compartment of the tumor cells, therby inhibiting proliferation or survival of the tumor cells. The term "mammal" is intended to encompass animal species that are susceptible to erbB2-overexpressing tumors and may include humans, monkeys, dogs, cats, rats, mice, etc. A nucleic acid molecule encoding an antibody homologue can be introduced into tumor cells in a mammal using one of a number of techniques suitable for introduction of exogenous DNA into cells in vivo.

The functional outcome of intracellular antibody expression on the subsequent expression and/or function of the protein targeted for antibody binding (referred to as the target protein) can be assessed by suitable assays that monitor the expression and/or function of the target protein. With regard in particular to erbB2, the effect of intracellular anti-erbB2 sFv expression can be examined using an erbB2 overexpressing epithelial carcinoma cell line, such as SKOV3, into which an anti-erbB2 sFv has been introduced in vitro. Cell surface expression of erbB2, or other membrane target protein, following intracellular antibody homologue expression can be assessed by standard immunohistochemistry techniques using an antibody specific for the target protein. The subcellular localization of the target protein and/or the antibody homologue can be determined, for example, by immunoelectron microscopy (e.g., the antibody homologue can be labeled with gold particles and the target protein with silver particles, or vice versa). Additionally, the effect of intracellular antibody expression on cellular proliferation can be assessed by immunohistochemistry using an antibody against a proliferation-associated antigen, such as the nuclear antigen Ki-67 (see Example 4). Alternatively, cell proliferation can be measured using commercially available cell proliferation assays (e.g., the Cell Titer 96 Aqueous Non-Radioactive Cell Proliferation Assay from Promega; see Example 4). The effect of intracellular anti-erbB2 expression on cell survival can be assessed by quantitating the number of stable cell clones obtainable after transfection of cells with the anti-erbB2 expression vector (see Example 5). As demonstrated in the Examples, intracellular anti-erbB2 sFv expression markedly reduces expression of erbB2 on the surface of an erbB2 overexpressing carcinoma cell line (SKOV3) and, moreover, markedly inhibits both cell proliferation and cell survival.

The functional outcome of intracellular anti-erbB2 antibody homologue expression on tumor cell growth and survival in a mammal can be assessed in vivo using animal model systems that may be predictive of therapeutic efficacy in humans. For example, carcinoma cells (e.g., SKOV3 cells) are transfected with the anti-erbB2 expression vector ex vivo and then transferred into mice (e.g., athymic nude mice). Tumor growth, as measured by tumor size, is monitored over time (e.g., 80 days), with reduced or absent tumor growth indicating that intracellular anti-erbB2 expression inhibits cell proliferation and/or survival (see Example 6). Carcinoma cells can also be modified in vivo to express an anti-erbB2 sFv intracellularly. Carcinoma cells (e.g., SKOV3) are first injected into the peritoneum of mice and then an adenovirus-polylysine DNA complex, comprising the anti-erbB2 sFv expression vector, is also injected into the peritoneum. Tumor growth can be monitored in vivo and/or carcinoma cells can be recovered from the animal and their survival assessed in vitro.

Compositions of the Invention

The invention provides isolated nucleic acid molecules encoding endoplasmic reticulum-expressed forms of anti-erbB2 antibody homologues. The term "isolated" as used herein refers to a nucleic acid substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived. The term "nucleic acid" is intended to encompass DNA and RNA and may be single or double-stranded. A preferred nucleic acid molecule comprises a first nucleotide sequence encoding a signal sequence operatively linked in a 5' to 3' direction by a phosphodiester bond to a second nucleotide sequence encoding a single chain Fv fragment that binds as erbB2 oncoprotein. The signal sequence directs expression of a protein (e.g., the anti-erbB2 sFv) comprising the signal sequence to an endoplasmic reticulum. Preferably, the signal sequence comprises an amino acid sequence shown in SEQ ID NO:3. Preferably, the anti-erbB2 sFv comprises an amino acid sequence shown in SEQ ID No:5, and is encoded by a nucleotide sequence shown in SEQ ID NO:4.

The invention further provides recombinant expression vectors comprising a nucleic acid molecule encoding an endoplasmic reticulum-expressed forms of an anti-erbB2 antibody homologue (e.g., an endoplasmic reticulum-expressed form of an anti-erbB2 sFv). As used herein, the term "vector" refers generally to a nucleic acid molecule capable of transporting another nucleic acid to which it has been linked. The term "recombinant expression vector" refers to a vector which is capable of directing expression of a nucleic acid to which it has been linked. The recombinant expression vector can be, for example, a plasmid vector or a viral vector.

The invention still further provides host cells into which a recombinant expression vector of the invention has been introduced. Preferably, the host cell is a mammalian cell, more preferably a malignant mammalian cell, preferably, an epithelial carcinoma cell. In various embodiments, the epithelial carcinoma cell may be of a tissue or organ selected from the group consisting of breast, ovary, gastrointestinal tract, lung and salivary gland.

Other Embodiments of the Invention

While the invention has been described in particular with regard to inhibition of erbB2 expression and function in tumor cells (e.g., carcinoma cells), the intracellular antibody approach described herein can equally be applied to other target proteins to modulate their expression and/or function. For example, antibody homologues against other cell surface receptors, such as receptor tyrosine kinases in addition to erbB2, can be expressed intracellularly in the endoplasmic reticulum to inhibit the surface expression and function of the receptor tyrosine kinases in accordance with the present invention. As described herein, endoplasmic reticulum-expressed forms of antibody homologues are prepared by linkage of nucleic acid encoding an appropriate signal sequence to nucleic acid encoding the antibody homologue. Examples of receptor tyrosine kinases that can be inhibited according to the invention include the epidermal growth factor receptor (EGFR), the platelet derived frowth factor receptor (PDGFR), the sis, fms and kit oncogene products and other kinases described in Hanks, S. K. et al. (1988) *Science* 241:42–52.

In addition to modulating the expression and/or function of cell surface membrane proteins by binding to their immature forms during transit through the endoplasmic reticulum, the endoplasmic reticulum-expressed forms of antibody homologues described herein can also be used to modulate the function of soluble, secreted proteins by binding to their intracellular forms during transit through the endoplasmic reticulum. Accordingly, in another embodiment, the invention provides a method for inhibiting the function of a soluble secreted protein by expressing intracellularly in the endoplasmic reticulum, an antibody homologue that binds to the secreted protein.

Furthermore, the invention is not limited to modulating the expression and/or function of endoplasmic reticulum-expressed proteins, but rather can also be applied to modulating the function of proteins found in other cellular locations. For example, an antibody homologue can be targeted intracellularly to the cytosol or the nuceus to modulate the function of cytosolic or nuclear proteins, respectively. To target an antibody homologue to the cytoplasm of a host cell, to thereby modulate the function of a cytosolic protein, a nucleic acid molecule encoding an antibody homologue which lacks a signal sequence is introduced into the host cell. Alternatively, to express an antibody homologue in the nucleus of a host cell, to thereby modulate the function of a nuclear protein, a nucleic acid molecule encoding a nuclear-targeted form of an antibody homologue is introduced into the host cell. A nucleotide sequence encoding a nuclear localization sequence (NLS) from a nuclear protein (e.g., from an SV40 T antigen) can be operatively linked to a nucleotide sequence encoding an antibody homologue to thereby target the antibody homologue to the nucleus when expressed in a mammalian host cell.

The following examples are given for the purpose of illustrating various embodiments of the invention and are not meant to limit the present invention in any fashion.

EXAMPLE 1

An Anti-erbB2 Single Chain antibody (sFv) Expression Vector

As a means to prevent maturational processing of the nascent erbB2 protein during synthesis, a gene construct was designed which encodes an anti-erbB2 single chain immunoglobulin (sFv) linked to a signal sequence. It was hypothesized that expression of this construct in target cells would result in an endoplasmic reticulum localized form of the sFv which would entrap erbB2 during synthesis thus preventing its subsequent translocation to the cell surface. The anti-erbB2 sFv construct is referred to herein as pGT21. As a control, a similar anti-erbB2 sFv construct was designed which lacked a signal sequence which would dictate its localication to the endoplasmic reticulum (referred to as pGT20). The pGT20 and pGT21 constructs are diagrammed schematically in FIG. 1. A third construct encoding an endoplasmic reticulum-form of a human anti-idiotype sFv (4B5) was also prepared as a control (this construct is referred to as pGT23).

Expression plasmids were derived containing gene constructs encoding single chain immunoglobulins directed aginst human erbB2. For this purpose, the eukaryotic expression vector pCDNA3 (obtained commercially from Invitrogen) was used. This vector drives transcription via the CMV early intermediate promoter/enhancer and conatins a neomycin resistance gene as a selective marker. The anti-erbB2 sFv plasmid, e23scFv (Batra, J. et al. (1992) *Proc. Natl. Acad. Sci. USA* 89:5867–5871) was obtained from Oncologix and used for the derivation of subsequent constructs. Genetic modifications of the anti-erbB2 sFvs were carried out empolying standard polymerase-chain reaction (PCR) methods. PCR was performed using Pfu polymerase (Stratagene) with the 5' primer: AGGGTACCATG-GACGTCCAGCTGACC (SEQ ID NO:1), and the 3" primer: GCTCTAGATTAGGAGACGGTGACCGTG-GTCC (SEQ ID NO:2). The PCR product, containing an ATG initiation codon followed by the sFv gene, was subject to digestion with the restriction endonucleases KpnI and XbaI, and cloned into pCDNA3. This construct, pGT20, would be predicted to express a non-endoplasmic reticulum (ER) form of the sFv, as the coding region lacks a signal sequence to achieve localization of the sFv to the endoplasmic reticulum. To ensure that the sFv was directed to the endoplasmic reticulum, the coding sequence for a leader peptide (amino acid sequence: MKSHSQVFVFLLLCVSGAHG) (SEQ ID NO:3) was incorporated into the 5" end of the anti-erbB2 sFv coding sequence by PCR methods. This PCR product was also cloned into the KpnI/XbaI sites of pCDNA3. This construct is named pGT21. The constructs were confirmed by standard dideoxy sequencing.

EXAMPLE 2

Transfection of Carcinoma Cells with Anti-erbB2 sFv Expression Vectors

To determine the effect of intracellular expression of anti-erbB2 sFv on cell surface erbB2 expression, cell proliferation and cell survival, the anti-erbB2 sFv expression vectors and control vector described in Example 1 were introduced into carcinoma cells. The human ovarian carcinoma cell lines, SKOV3 and SW626, and the human epithelial carcinoma cell line HeLa were obtained from the American Type Culture Collection (Rockville, Md.). Cells were maintained in complete medium consisting of Dulbecco's modified Eagles medium (DMEM) supplemented with L-glutamine (300 μg/ml), penicillin (100 I.U./ml), streptomycin (25 μg/ml) and 10% fetal calf serum (PAA) at 37° C. in a humidified 5% $CO_2$ atmosphere. The SKOV3 ovarian carcinoma cell line is known to overexpress the erbB2 protein on its surface. The SW626 ovarian carcinoma cell line is also known to overexpress cell surface erbB2, however not at the same magnitude as for the SKOV3 cell line. The HeLa epithelial carcinoma cell line does not overexpress cell surface erbB2.

For transient transfection of cells, the method of adenovirus-polylysine was employed (Curiel, D. T. et al. (1992) *Human Gene Therapy* 3:147–154). Adenovirus-polylysine (AdpL) was prepared by linkage of the replication defective adenovirus dl1014 to poly-L-lysine (Sigma) by the EDC method (Cristiano, R. J. et al. (1993) *Proc. Natl. Acad. Sci. USA* 90:11548–11552). Viral-polylysine conjugates were diluted to a concentration of $1 \times 10^{11}$ viral particles per ml. Conjugate-DNA complexes were then formed by the sequential addition of 100 μl of AdpL, 6.0 μg of plasmid DNA diluted in 200 μl 150 mM NaCl, 20 mM HEPES, pH 7.3 (HBS) and 4.0 μg poly-L-lysine (from Sigma Chemical Co., St. Louis, Mo.) diluted in 200 μl HBS. A volume of conjugate-DNA complex containing 2.0 μg of plasmid DNA was then delivered to target cells in 6 well tissue culture dishes in 1.0 ml of medium containing 2% fetal calf serum. Incubation was carried out for 1 hour at 37° C., after which 2 ml of complete medium was added to cells and incubation continued for 48, 72, or 96 hours. The adenovirus-polylysine-DNA complexes containing a β-galactosidase reporter gene (pCMVβ) led to detectable levels of reporter gene expression in >90% of targeted cells.

Plasmid DNAs were stably transfected into target cells by the lipofectAMINE method (GIBCO/BRL, Grand Island, N.Y.) using conditions described by the namufacturer. Briefly, lipid/DNA complexes consisting of 40 μg lipofectAMINE and 4.0 μg plasmid DNA were delivered to cells at ~50% confluency in 6.0 cm tissue culture dishes in a volume of 1.0 ml of OptiMEM medium (GIBCO/BRL). After an 18 hour incubation, the transfection medium was removed and replaced with complete medium and incubation continued for an additional 48 hours. Cells were then split into selective medium containing Geniticin (GIBCO/BRL) at 1 mg/ml. The cells ere maintained for 21 days at which time the number of resistant colonies was determined by standard crystal violet staining.

EXAMPLE 3
Downregulation of Cell Surface erbB2 Expression on Ovarian Carcinoma Cells by Intracellular Expression of Anti-erbB2 sFv The plasmid DNAs pCDNA3, pGT20, and pGT21 were transfected into the erbB2 over-expressing ovarian carcinoma cell line SKOV3 using the adenovirus-polylysine (AdpL) method. At various times after transfection, the cells ere evaluated for cell surface expression of erbB2 using the technique of immunocytochemistry empolying an anti-human erbB2 monoclonal antibody as follows: $5 \times 10^4$ cells were cytocentrifuged onto superfrost slides (Fisher) and fixed for 10 minutes in 4% paraformaldehyde in TBS (Tris-buffered saline). After appropriate blocking steps, a rabbit anti-human cerbB2 antibody (DAKO) was employed at the manufacturers' pre-diluted concentration and an ABC peroxidase system (Vector Labs) was utilized for immunocytochemical detection of cell surface c-erbB2-protein.

Figure 2A:
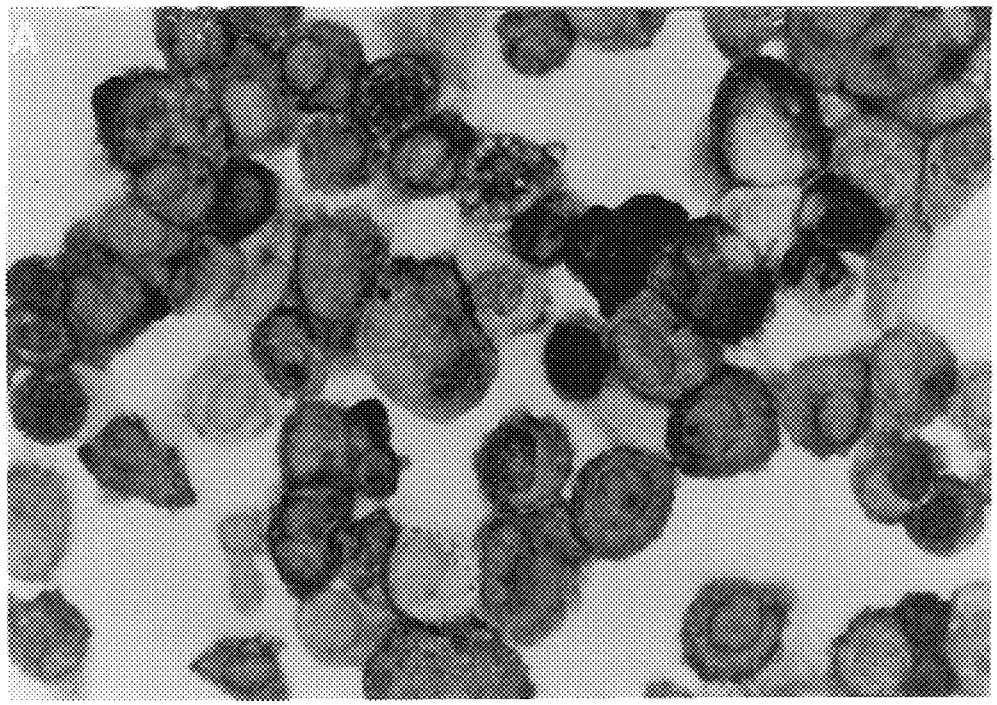
FIGS. 2A–C are photographs of immunocytochemistry slides of human ovarian carcinoma SKOV3 cells reacted with a rabbit anti-human anti-erbB2 sFv expression on cell surface expression of erbB2 protein.
Figure 2B:
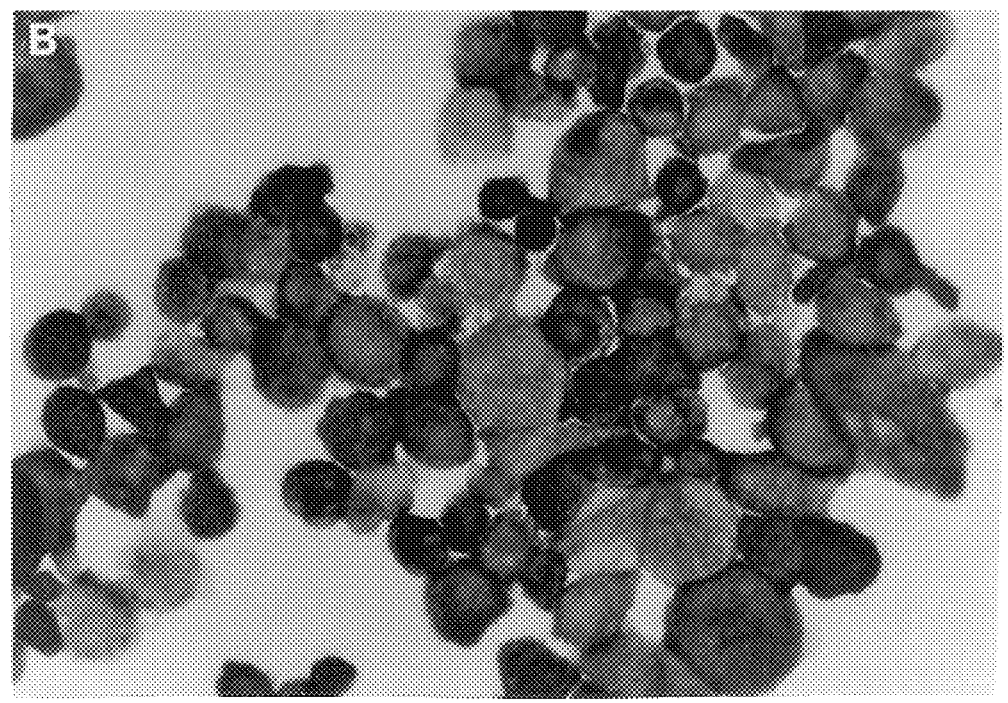
Figure 2C:
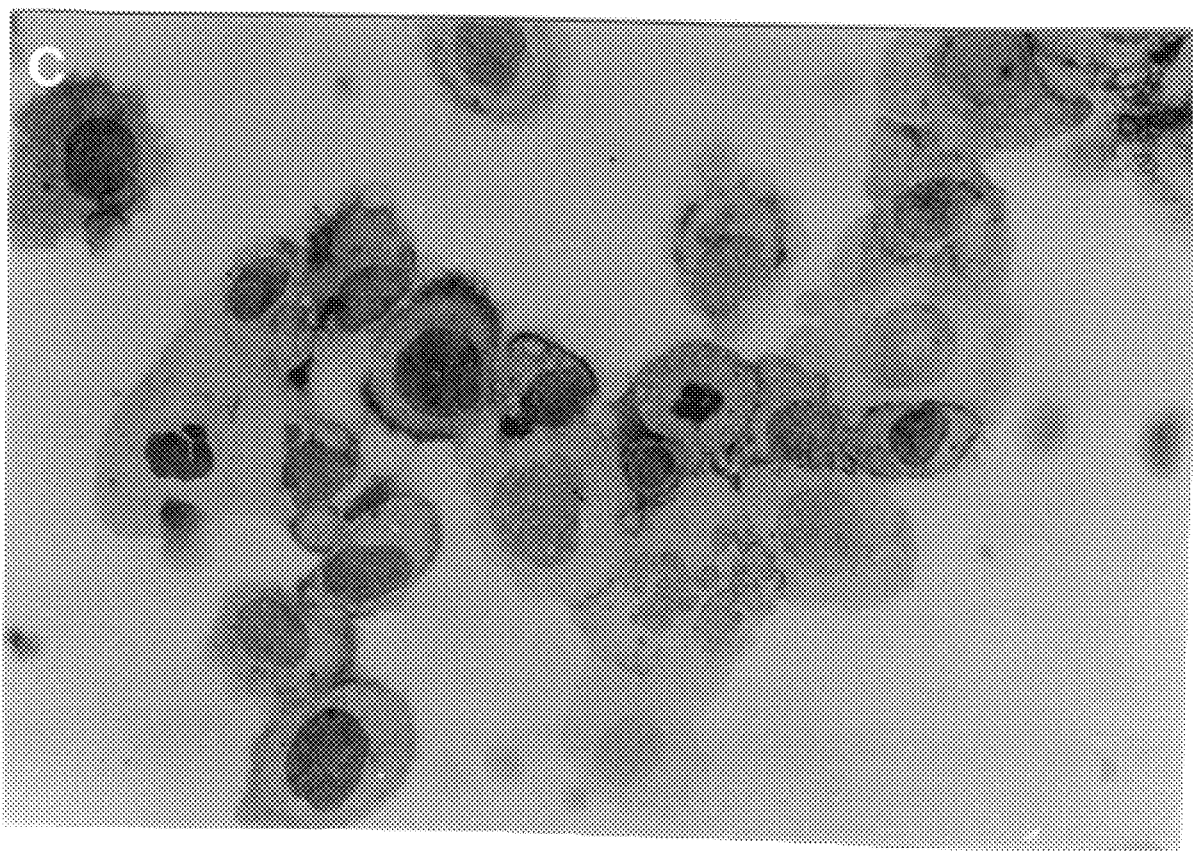

The results of the immunocytochemistry assays are shown in FIGS. 2A–2C. SKOV3 cells transfected with the irrelevant plasmid DNA pCDNA3 exhibited high levels of cell surface erbB2, as would be expected (FIG. 2A). Additionally, SKOV3 cells transfected with the non-endoplasmic reticulum form of the anti-erbB2 sFv (pGT20) exhibited levels of cell surface erbB2 similar to the control (FIG. 2B). In contrast, SKOV 3 cells transfected with pGT21, which encodes an endoplasmic reticulum form of the anti-erbB2 sFv, demonstrated marked down-regulation of cell surface erbB2 expression (FIG. 2C). This downregulation appeared to be time-dependent, with cell surface erbB2 levels progressively declining from 48 to 96 hours post-transfection. At 96 hours post-transfection, fewer than 10% of the pGT21 transfected cells exhibited detectable levels of cell surface erbB2 protein. The cells otherwise appeared morphologically indistinguishable from the control groups.

To exclude the possibility that anti-erbB2 sFv secreted by transfected cells could exert a "paracrine effect" on non-transfected cells, additional experiments were performed. SKOV3 cells were transfected with pCDNA3, pGT20 and PGT21. After 72 hours, supernatant was collected and delivered to non-transfected SKOV3 cells which were than analyzed for cell surface erbB2 expression by immunocytochemistry. In this analysis, none of the transfected cell supernatants exhibited the capacity to down-regulate cell surface erbB2 expression. Thus, intracellular expression of an anti-erbB2 sFv is capable of effective down-modulation of cell surface erbB2. The fact that only the endoplasmic reticulum form of the erbB2 sFv was capable of achieving this effect is consistent with the nascent erbB2 being entrapped in the endoplasmic reticulum during synthesis.

EXAMPLE 4
Inhibition of Proliferation of Ovarian Carcinoma Cells by Intracellular Expression of Anti-erbB2 sFv To determine whether cell surface expression of erbB2 correlates with cellular proliferation rates, the effect of the various sFv gene constructs on tumor cell proliferation was evaluated. For this analysis, immunocytochemistry for the proliferation-associated nuclear antigen Ki-67 was employed. A mouse monoclonal antibody which recognizes an epitope on the proliferating cell antigen Ki-67, in combination with an alkaline phosphate system (APAAP-DAKO) was used for immunocytochemical detection of cell proliferation. The experiments described in this Example were performed in parallel with those for detection of cell surface erbB2 described in Example 3. For further description of the use of the Ki-67 antigen to analyze cell proliferation see Gerdes, J., et al. (1984) *J. Immunol.* 133:1710–1715.

Figure 3A:
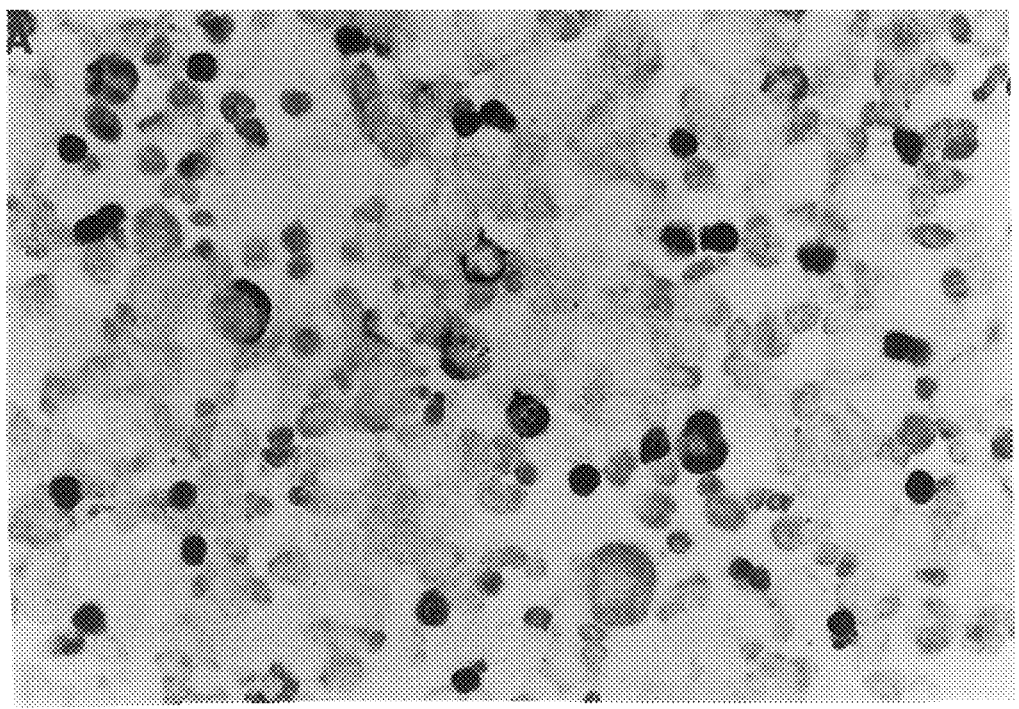
FIGS. 3A–C are photographs of immunocytochemistry slides of human ovarian carcinoma SKOV3 cells reacted with a mouse anti-Ki-67 monoclonal antibody, depicting the effect of intracellular anti-erbB2 sFv expression on nuclear expression of the proliferation-associated marker Ki-67.
Figure 3B:
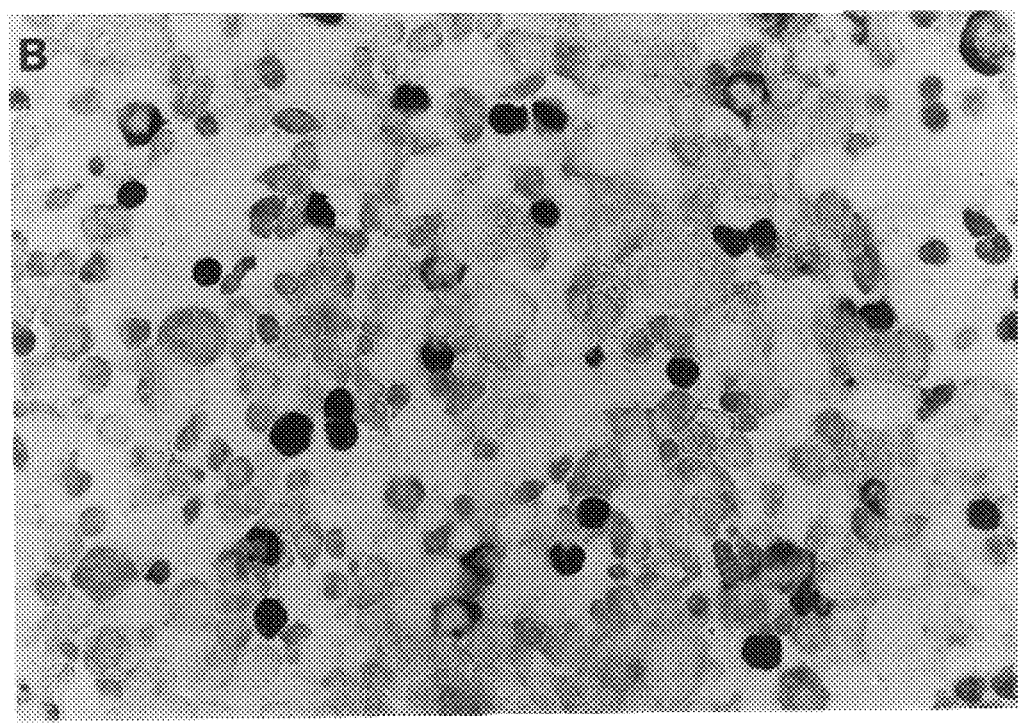
Figure 3C:
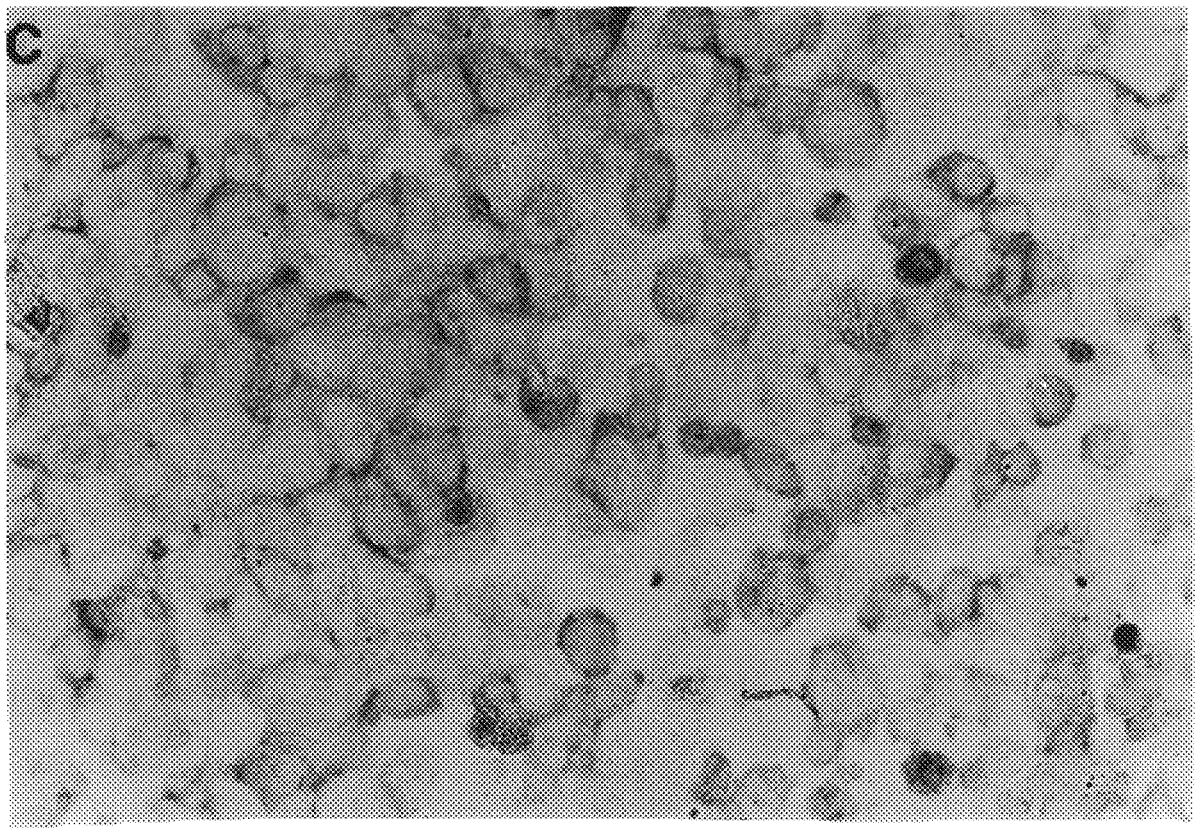

The results of the cell proliferation immunocytochemistry assays are shown in FIGS. 3A–C. Transfection of SKOV3 cells with the control plasmid pCDNA3 resulted in the immunocytochemical detection of active cellular proliferation (FIG. 3A). In addition, transfection with the non-endoplasmic reticulum form of the anti-erbB2 sFv (pGT20) did not result in any net change in cell proliferation (FIG. 3B). In marked contrast, transfection of the erbB2 over-expressing cell line SKOV3 with the endoplasmic reticulum form of the anti-erbB2 sFv (pGT21) resulted in a dramatic inhibition of cellular proliferation as determined by Ki-67 immunohistochemistry (FIG. 3C). The percentage of cells exhibiting nuclear staining in this group was significantly reduced, paralleling the percentage decrease of cell surface erbB2 protein.

The degree of inhibition of cell proliferation was also assessed employing a quantitative assay. Quantitative assessment of cell proliferation was carried out using the Cell Titer 96 Aqueous Non-Radioactive Cell Proliferation Assay (Promega) using conditions recommended by the manufacturer. For this analysis, target cells were plated (5000 cells/well) and transfected with the various plasmid constructs using the AdpL method. After a 96 hour incubation, the transfected cells were analyzed for released formazan by measuring absorbance at 490 nm using an ELISA plate reader. A standard curve was derived in parallel for each analysis by linear dilutions of non-transfected cells. Control studies established a linear relationship between the number of proliferative cells and the concentration of formazan released.

Figure 4:
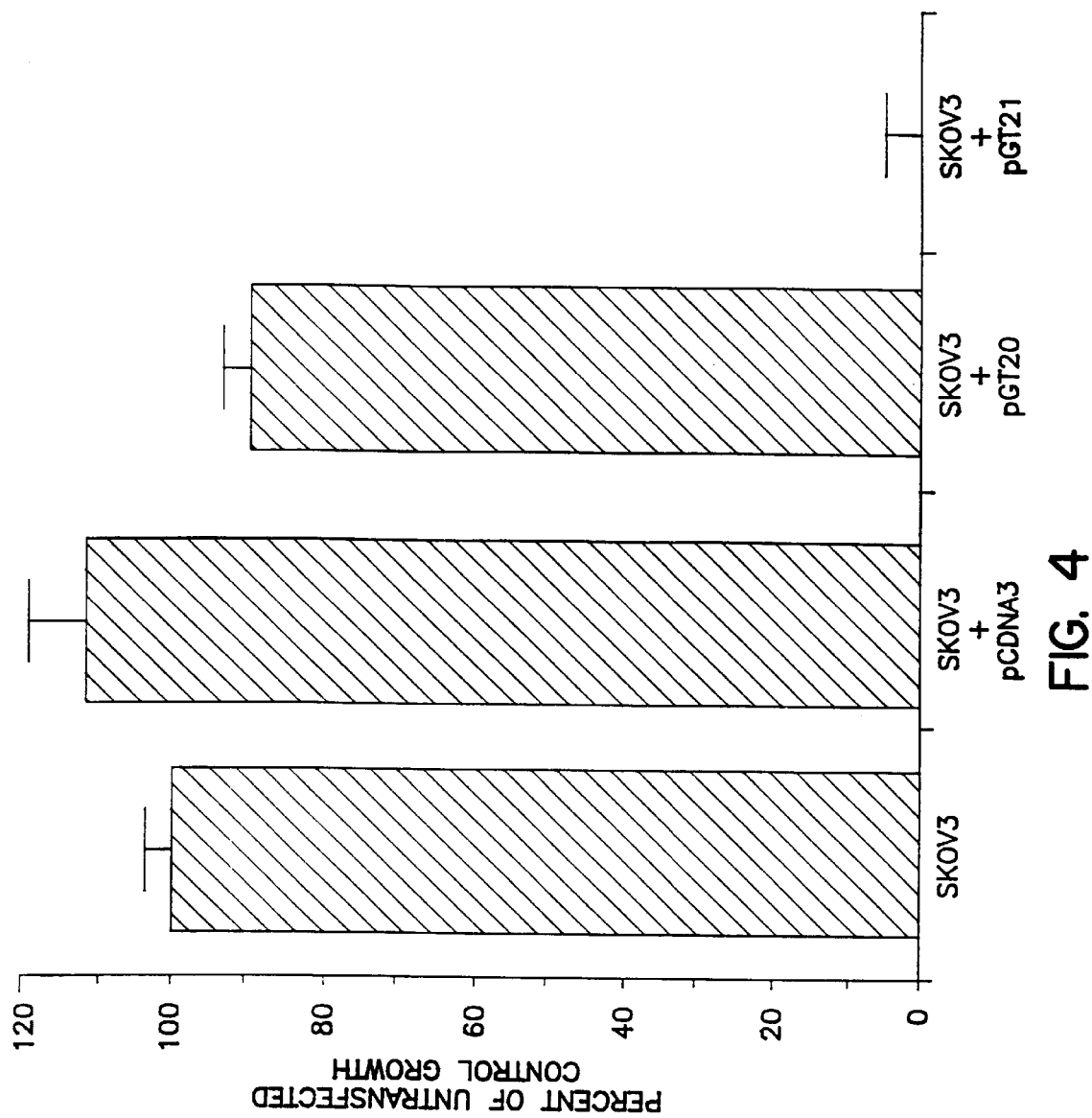
FIG. 4 is a graphic representation of the effect of intracellular expression of an endoplasmic reticulum form of anti-erbB2 sFv (pGT21) on cellular proliferation of SKOV3 cells, as compared to the effect of intracellular expression of a non-endoplasmic reticulum form of anti-erbB2 (pGT20) or a control plasmid (pCDNA3). The index of cellular proliferation was determined and compared to untransfected control cells. Experiments were performed ×12 each and results reported as mean ±S.E.

The cell proliferation results for transfected cells using the quantitative assay described above are shown graphically in FIG. 4. Transfection of SKOV3 with the control plasmid pCDNA3 did not affect the measured index of cellular proliferation compared to non-transfected control cells (p=0.103). Additionally, the measured index of cellular proliferation in cells transfected with the non-endoplasmic reticulum form of the anti-erbB2 sFv did not significantly differ from these two controls (p=0.118). Transfection of SKOV3 with the endoplasmic reticulum form of the anti-erbB2 sFv, however, resulted in a very significant inhibition of cellular proliferation (p<0.001). Extrapolation of the measured absorbance against the standard curve indicated that cellular proliferation was inhibited more than 95% compared to the control groups. Thus, the expression of the endoplasmic reticulum form of the anti-erbB2 sFv inhibits proliferation of erbB2 over-expressing tumor cells. The level of down-regulation of cell surface erbB2 mediated by the endoplasmic reticulum form of the anti-erbB2 sFv paralleled the magnitude of the observed anti-proliferative effects.

EXAMPLE 5
Reduction in Survival of Ovarian Carcinoma Cells by Intracellular Expression of Anti-erbB2 sFv As the endoplasmic reticulum-expressed anti-erbB2 sFv exhibited such a prominent anti-proliferative effect (Example 4), it also exhibited a direct tumoricidal effect in cells stably modified to express this gene construct. Since the plasmids pCDNA3, pGT20 and pGT21 contained neomycin selectable markers, they were used to derive stable clones as described in Example 2.

As a preliminary control, the various plasmid contructs were used to derive G418 resistant clones in HeLa, a cancer cell line not characterized by over-expression of erbB2. After selection, the number of HeLa clones derived from transfection with pGT20 and pGT21 was not significantly different (see Table 1 below). Further, this number of clones was not significantly different when HeLa cells were transfected with the control plasmid pCDNA3.

A similar analysis was then carried out with the erbB2 over-expressing tumor line SKOV3 as the target. The number of clones derived with pGT20, the non-endoplasmic reticulum anti-erbB2 sFv, did not differ from the number derived with the control plasmid pCDNA3. Transfection with pGT21, however, resulted in a dramatic reduction in the number of stable clones derived (p<0.001). The ER form of the anti-erbB2 sFv was incompatible with long-term viability of transfected SKOV3 cells. Further, this effect appeared specific for erbB2 over-expressing cells.

A similar analysis was carried out on another tumor target, the ovarian carcinoma cell-line SW626. The endoplasmic reticulum anti-erbB2 sFv also showed a significant reduction in the number of stable clones derived compared to the non-ER form of the anti-erbB2 sFv (p=0.020). The magnitude of this effect, however, was substantially less than that observed for SKOV3. It thus appears that the level of anti-neoplastic effect achieved by the anti-erbB2 sFv correlated with the level of cell surface erbB2 over-expression on target cells.

TABLE 1

Derivation of Stable Colonies after Transfection of Epithelial Carcinoma Cell Lines with anti-erbB2 sFv Expression Plasmids

| | G418 Resistant Colonies | |
|---|---|---|
| Cell Line | anti-erbB2 sFv non-ER form (pGT20) | anti-erbB2 sFv ER-form (pGT21) |
| SKOV3 | 36 | 5 |
| | 28 | 5 |
| | 23 | 3 |
| | 26 | 3 |
| | 27 | 3 |
| SW626 | 21 | 18 |
| | 24 | 16 |
| | 21 | 16 |
| | 28 | 21 |
| | 20 | 19 |
| HeLa | 68 | 77 |
| | 84 | 83 |
| | 91 | 93 |
| | 77 | 69 |
| | 88 | 89 |

To exclude the possibility that the basis for this effect could be non-specific endoplasmic reticulum (ER) localization of heterologous protein in transfected cells, similar experiments were carried out using the endoplasmic reticulum form of an sFv encoding an erbB2 irrelevant epitope (4B5). The results are shown below in Table 2.

TABLE 2

Derivation of Stable Colonies after Transfection of Epithelial Carcinoma Cell lines with Endoplasmic Reticulum (ER) Forms of anti-erbB2 and anti-4B5 sFv Expression Plasmids

| Cell Line | ER form of anti-erbB2 sFv (pGT21) | ER form of anti-4B5 sFv (pGT23) |
|---|---|---|
| SKOV3 | 3 | 11 |
| | 5 | 18 |
| | 3 | 16 |
| | 0 | 10 |
| | 2 | 16 |

For SKOV3, the number of stable clones derived employing the anti-4B5 sFv construct did not significantly differ from the number observed with employment of the control plasmid pCDNA3 (p=0.09). Thus, the observed anti-neoplastic effect of the endoplasmic reticulum from of the anti-erbB2 sFv was on the basis of its encoded antigen spcificity, and not a non-specific effect related to perturbation of a sub-cellular compartment.

Figure 5:
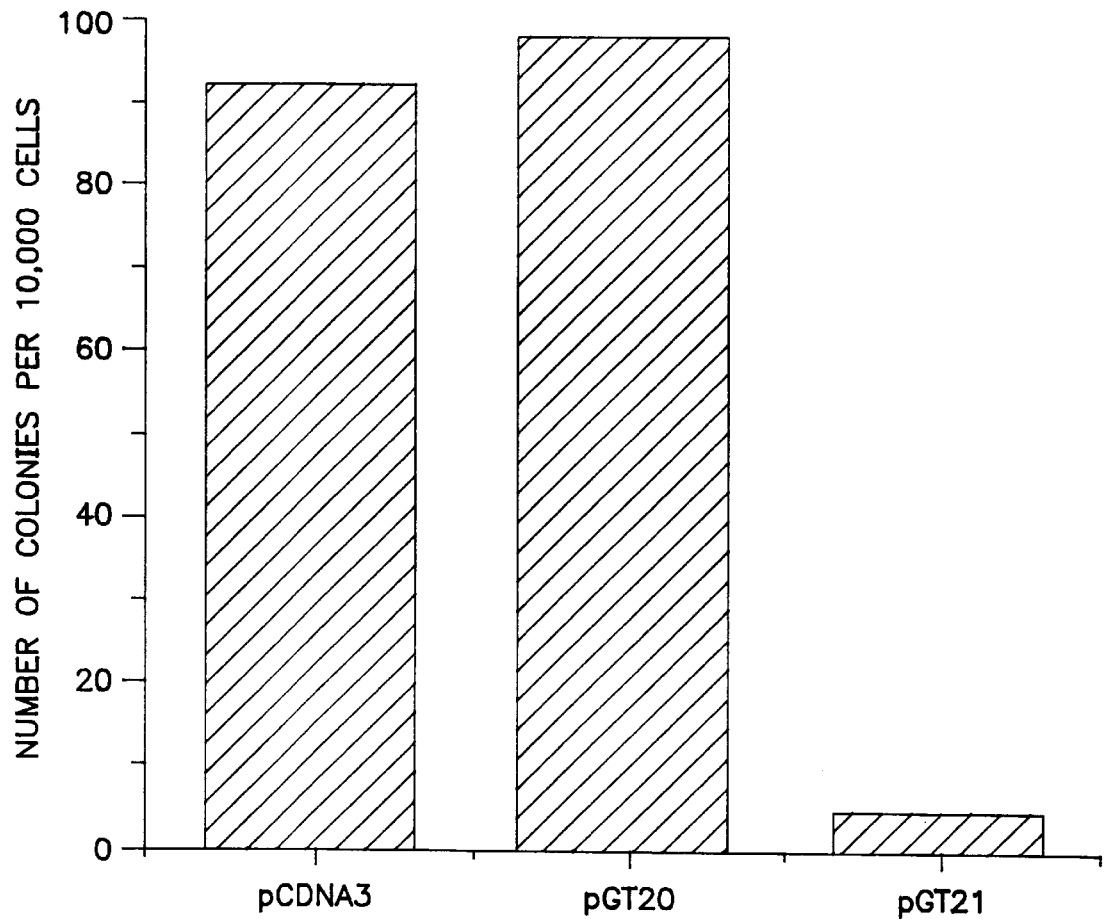
FIG. 5 is a graphic representation of the effect of intracellular expression of an endoplasmic reticulum form of anti-erbB2 sFv (pGT21) on growth of SKOV3 cells in soft agar, as compared to the effect of intracellular expression of a non-endoplasmic reticulum form of anti-erbB2 (pGT20) or a control plasmid (pCDNA3).
Figure 6:
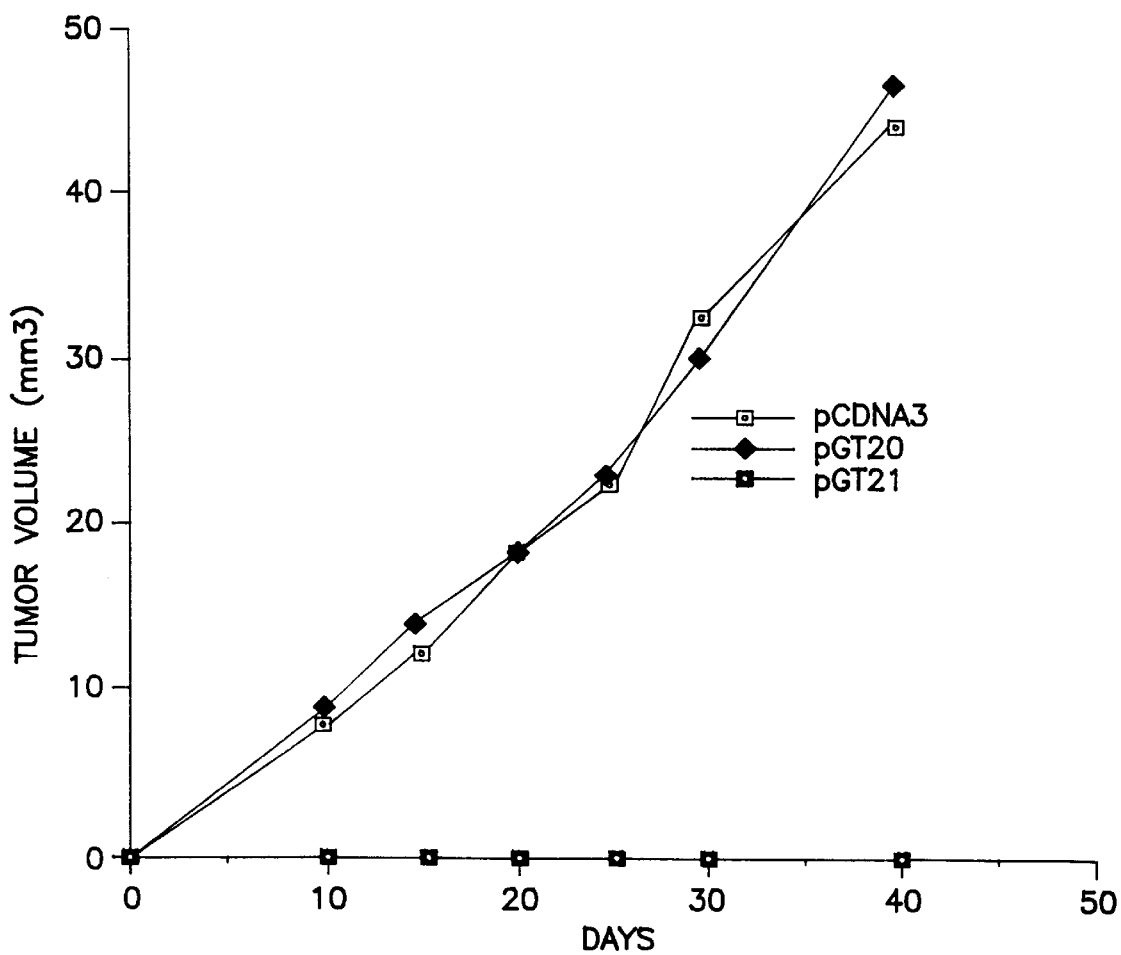
FIG. 6 is a graphic representation of the effect of intracellular expression of an endoplasmic reticulum form of anti-erbB2 sFv (pGT21) on tumorigenicity of SKOV3 cells transplanted subcutaneously into nude mice, as compared to the effect of intracellular expression of a non-endoplasmic reticulum form of anti-erbB2 (pGT20) or a control plasmid (pCDNA3).

EXAMPLE 6
Reduced Tumorigenicity of Ovarian Carcinoma Cells Transfected to Express Anti-erbB2 sFv Intracellularly The ability of intracellular expression of an anti-erbB2 sFv in SKOV3 cells to inhibit the tumorigenicity of the cells was examined. The growth of SKOV3 cells transfected with either pCDNA3 (control plasmid), pGT20 (non-endomplasmic reticulum form of anti-erbB2 sFv) or pGT21 (endoplasmic reticulum form of anti-erbB2 sFv) in soft agar was assayed by standard techniques. The ability of cells to form colonies in soft agar (i.e., anchorage independent growth) was used as an indicator of their tumorigenicity. The results of the experiment are shown in FIG. 5. Only the endoplasmic reticulum form of anti-erbB2 sFv (pGT21) was able to inhibit growth of transfected SKOV3 cells in soft agar, as compared to the pCDNA3 control plasmid. Transfection of SKOV3 cells with pGT21 inhibited colony formation by greater than 95%.

As an additional, independent index of anchorage independent growth, tumor formation was evaluated in athymic nude mice. SKOV3 cells transfected with either pCDNA3, pGT20 or pGT21 were transplanted subcutaneously into nude mice. Tumor growth was assessed by measuring tumor size (i.e., greater than 40 days post transplantation). These findings, in addition to the results of the soft agar growth assay, indicate that the endoplasmic reticulum form of the anti-erbB2 sFv was capable of abrogating the tumorigenicity of erbB2-overexpressing malignant cells.

Figure 7:
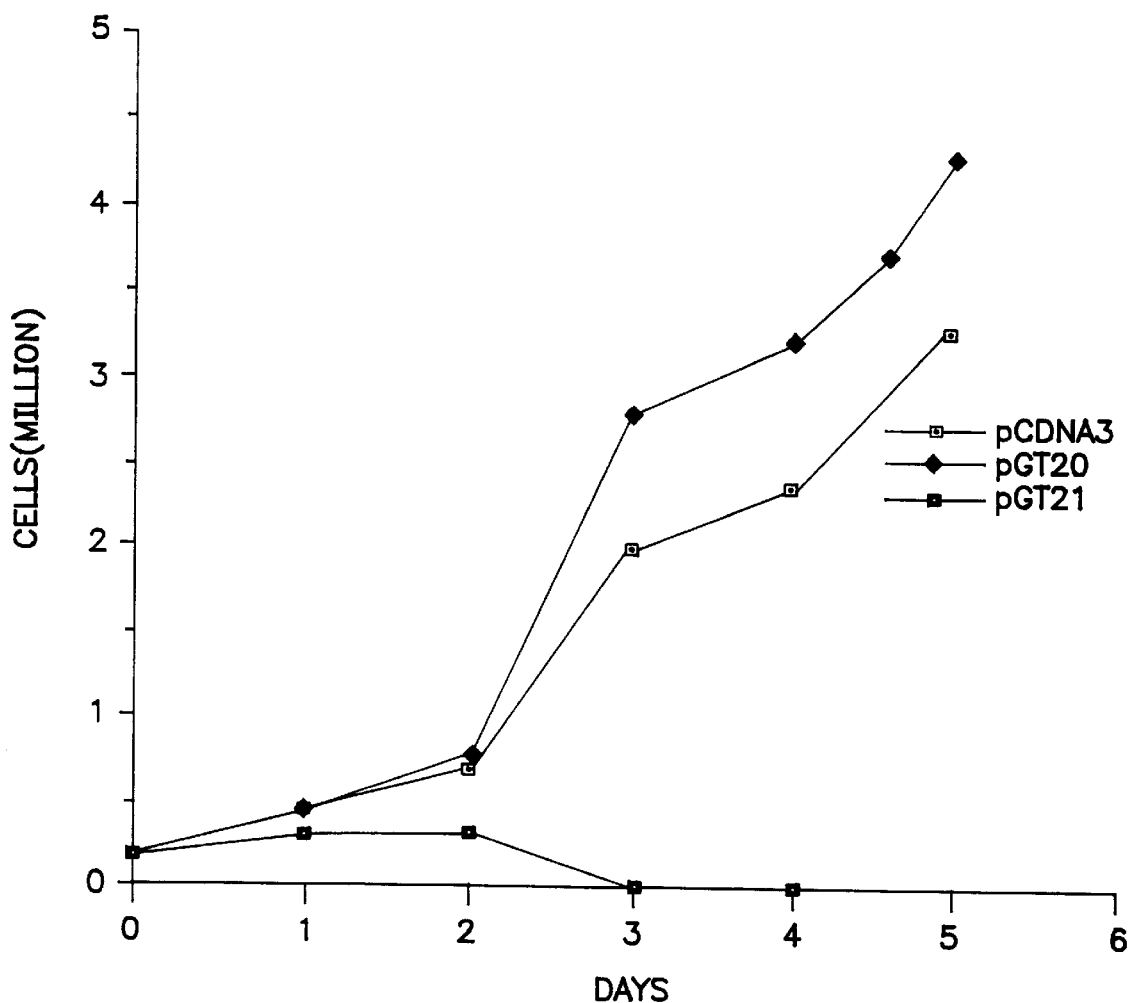
FIG. 7 is a graphic representation of the growth curves of SKOV3 cells transfected with an expression vector encoding an endoplasmic reticulum form of anti-erbB2 sFv (pGT21), a non-endoplasmic reticulum form of anti-erbB2 sFv (pGT20) or a control plasmid (pCDNA3).
Figure 8:
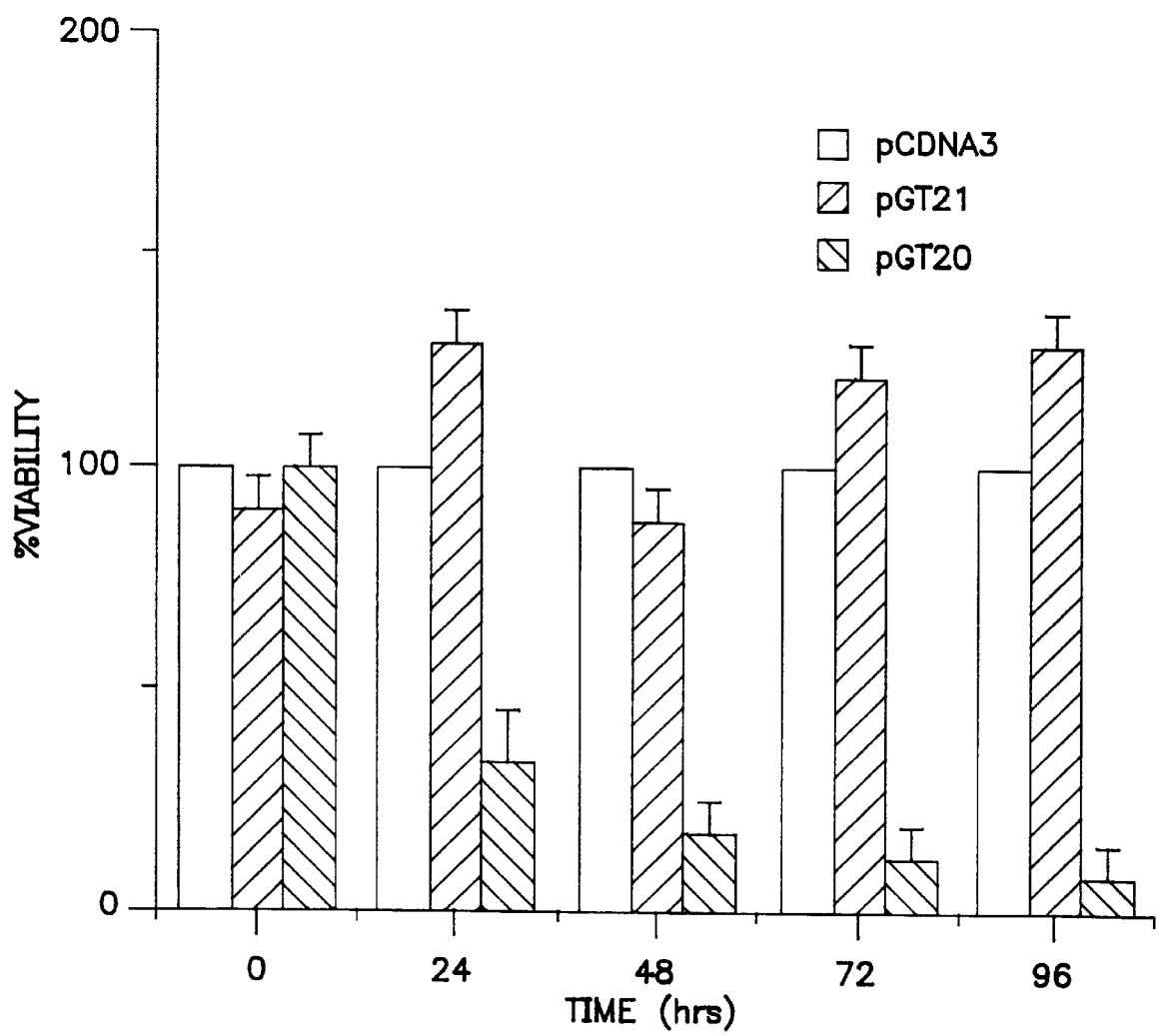
FIG. 8 is a graphic representation of the effect of intracellular expression of an endoplasmic reticulum form of anti-erbB2 sFv (pGT21) on cell viability of SKOV3 cells 24, 48, 72 or 96 hours after transfection, as compared to the effect of intracellular expression of a non-endoplasmic reticulum form of anti-erbB2 (pGT20) or a control plasmid (pCDNA3).

To determine the basis of this effect, cell growth parameters in response to intracellular expression of the endoplasmic reticulum form of anti-erbB2 sFv (pGT21), compared to control plasmids (pCDNA3 and pGT20) were evaluated. First, cell growth curves were determined over a 6 day period. The results are illustrated graphically in FIG. 7, in which cell number in millions is plotted against time in days. Transfection of the SKOV3 cells with either pCDNA3 or pGT20 did not affect the normal temporal increase in cell number. In contrast, tumor cell number decreased with time in the pGT21 transfected group. This analysis suggested that pGT21 transfection not only inhibited proliferation of the SKOV3 cells but also eradicated viable cells. To establish this, SKOV3 cells were transfected with either pCDNA3, pGT20 or pGT21 and at various time points after transfection (e.g., 24, 28, 72 and 96 hours) cell viability was directly evaluated employing an MTT assay for cell viability. The results are shown in FIG. 8. Neither pCDNA3 nor pGT20 exhibited an effect on cell viability. In contrast, cell viability was dramatically diminished upon transfer of the pGT21 construct. For example, at 96 hours post-transfection, greater than 95% of the SKOV3 cells were non-viable (i.e., had been killed). This indicates that the inhibition of erbB2 by the intracellular anti-erbB2 sFv was lethal to the SKOV3 cells. Thus, the specificity of the effect observed for anti-erbB2 inhibition of erbB2 can be exploited for selective killing of target cancer cells.

Figure 9:
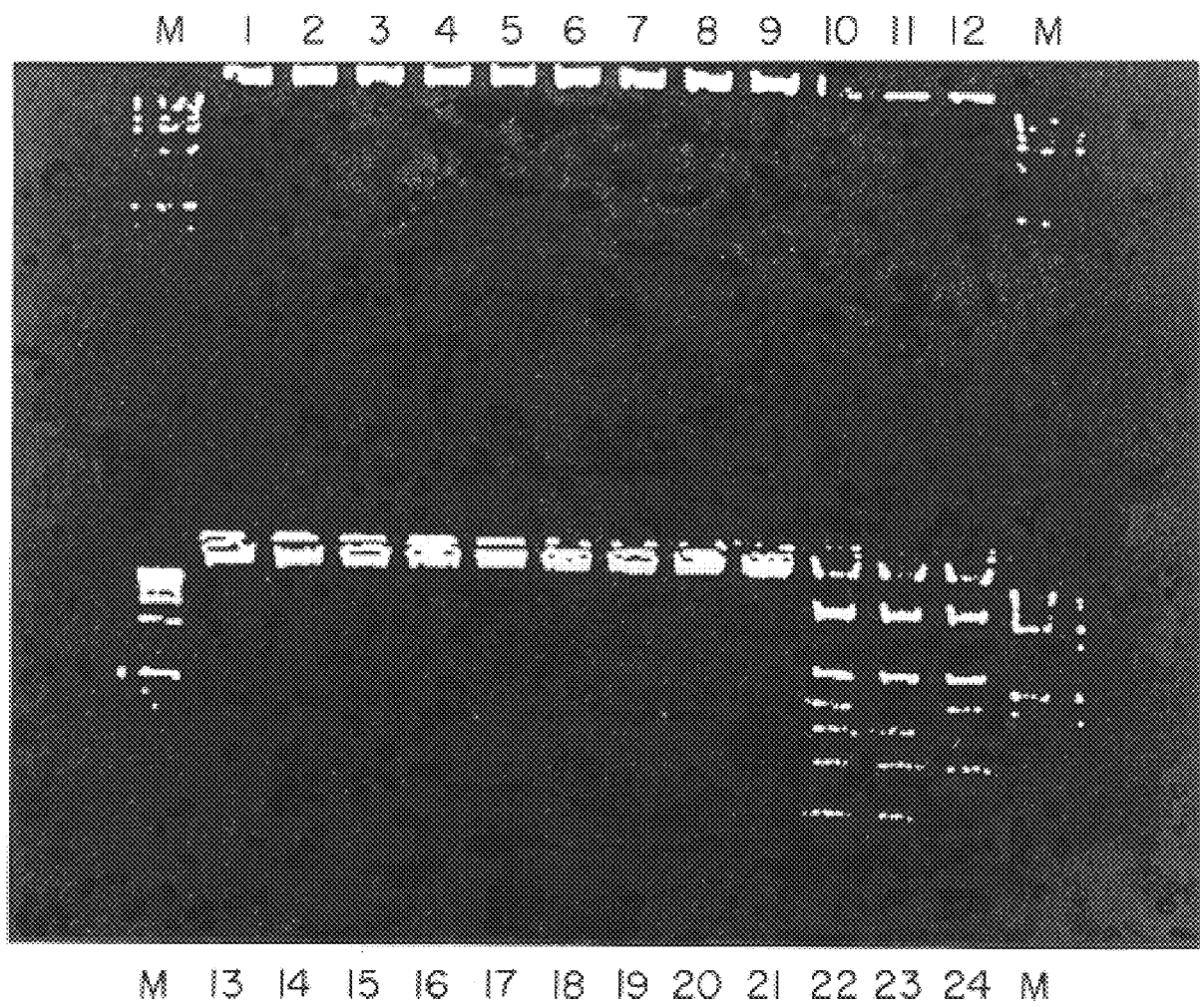
FIG. 9 is a photograph of an agarose gel depicting DNA fragmentation in SKOV3 cells folowing intracellular expression of an endoplasmic reticulum form of anti-erbB2 sFv.

To examine the basis of the effect of the intracellular endoplasmic reticulum form of anti-erbB2 sFv on cell viability, assays measuring apoptosis (or programmed cell death) were performed. DNA fragmentation was used as an indicator of apoptosis. SKOV3 or HeLa cells were transfected with pCDNA3, pGT20 or pGT21 and at various time points after transfection (e.g., 24, 48, 72 and 96 hours), DNA fragmentation was assessed by agarose gel electrophoresis of ethidium bromide stained DNA. FIG. 9 depicts a photograph of an agarose gel. Lanes 1–4 are HeLa cells 24 hours (lane 1), 48 hours (lane 2), 72 hours (lane 3) or 96 hours (lane 4) after transfection with pCDNA3; lanes 5–8 are HeLa cells 24 hours (lane 5), 48 hours (lane 6), 72 hours (lane 7) or 96 hours (lane 8) after transfection with pGT20; lanes 9–12 are HeLa cells 24 hours (lane 9), 48 hours (lane 10, 72 hours (lane 11) or 96 hours (lane 12) after transfection with pGT21; lanes 13–16 are SKOV3 cells 24 hours (lane 13), 48 hours (lane 14), 72 hours (lane 15) or 96 hours (lane 16) after transfection with pCDNA3; lanes 17–20 are SKOV3 cells 24 hours (lane 17), 48 hours (lane 18), 72 hours (lane 19) and 96 hours (lane 20) after transfection with pGT20; lanes 21–24 are SKOV3 cells 24 hours (lane 21), 48 hours (lane 22), 72 hours (lane 23) and 96 hours (lane 24) after transfection with pGT21; lanes marked M are size markers. No DNA fragmentation was observed in HeLa cells transfected with any of the contructs (lanes 1–12) or in SKOV3 cells transfected with either pCDNA3 or pGT20 (lanes 13–20). However, prominent DNA fragmentation was induced in SKOV3 cells transfected with pGT21 (lanes 21–24). Thus, the effect of erbB2 inhibition by intracellular expression of an endoplasmic reticulum form of anti-erbB2 sFv is to trigger apoptosis in erbB2 overexpressing tumor cells. In summary, Examples 3, 4, 5 and 6 demonstrate that expression intracellularly of an endoplasmic reticulum-expressed form of anti-erbB2 sFv in an erbB2 overexpressing carcinoma cell (e.g., the ovarian carcinoma cell line SKOV3) results in decreased cell surface expression of erbB2, decreased cellular proliferation, decreased cell survival and decreased tumorigenicity.

EXAMPLE 7

Cell Lines

The human breast carcinoma cell lines MDA-MB-361, BT-474, SK-BR-3, and MCF-7 were provided by Dr. Janet Price (Baylor University, Houston, Tex.). The MDA-MB-231 human breast carcinoma cell line was obtained from Dr. Andrew Kraft (University of Alabama at Birmingham, Birmingham, Ala.). The cell lines MDA-MB-361, BT-474, MCF-7, and MDA-MB-231 were cultured in Dulbecco's Modification of Eagle's Medium/Hams F12 medium (DMEM/F12) (Mediatech, Herndon, Va.), supplemented with 10% fetal calf serum (FCS) (PAA, Newport Beach, Calif.), L-glutamine (300 μg/ml), penicillin (100 i.μ./ml) and streptomycin (25 μg/ml). The SK-BR-3 cells were maintained in McCoy's 5A medium with the aforementioned supplements. All cell lines were incubated at 37° C. in a humidified 5% carbon dioxide atmosphere.

EXAMPLE 8

Viral Infections

E1 A/B-deleted replication-incompetent recombinant adenoviruses were obtained in the following ways: the adenovirus encoding β-galalctosidase (AdCMVLacZ) was provided by Dr. De-chu Tang (University of Alabama at Birmingham, Birmingham, Ala.). The adenovirus encoding the endoplasmic reticulum directed anti-erbB-2 sFv (Ad21) was constructed using homologous recombination techniques (Feng M, et al., Cancer Res. 1995; 55:2024–2028). Each adenovirus was delivered to the breast cancer cell lines at a multiplicity of infection of 100 plaque forming units (pfu) per cell. Cells were infected in reduced serum medium (DMEM with 2% FCS) for 90 minutes, then supplemented with normal culture medium and maintained until ready for analysis.

EXAMPLE 9

Immunohistochemistry

To determine the presence of cell surface erbB-2, immunohistochemistry with a human anti-erbB-2 antibody was employed. For this analysis, cells were seeded into six-well tissue culture plates (Nunc, Naperville, Ill.) at approximately 70% confluency. The cells were transduced with either the control adenovirus, AdCMVLacZ, or the endoplasmic reticulum directed anti-erbB-2 sFv encoding adenovirus, Ad21, as described above. Twenty-four hours post-infection, cells were fixed with 4% paraformaldehyde in 1×PBS (Phosphate Buffered Saline, pH 7.2) at 4° C. for 15 minutes. A rabbit anti-human c-erbB-2 antibody (DAKO, Carpinteria, Calif.) was then applied to the cells and used in conjunction with a Vectastain ABC peroxidase system (Vector Laboratories, Burlingame, Calif.) to detect cell surface erbB-2 protein.

EXAMPLE 10
Quantification of breast cancer cell viability

The anti-tumor effect of the anti-erbB-2 sFv was evaluated employing an assay of cell viability. For this analysis, all breast cancer cell lines were seeded at a density of $5 \times 10^3$ cells per well in 96 well plates (Costar, Cambridge, Mass.). Twenty hours later, either AdCMVLacZ, as a control, or Ad21 was delivered to the cells as described above. At 96 hours post-infection, direct analysis of cell viability was measured using the Cell Titer 96 AQ Non-Radioactive Cell Proliferation Assay (Promega Corp., Madison, Wis.). This assay is based on the ability of only viable cells to reduce 3-(4,5-dimethylthiazol-2-yl)-5-(3-carboxymethoxyphenyl)-2-(4-sulfophenyl)-2H-tetrazolium (MTS) to formazan that is soluble in tissue culture medium and can be measured spectrophotometrically at an absorbance of 490 nm. MTS solution (2 mL) was mixed with 100 $\mu$l of phenazine methosulfate (PMS) immediately before addition to the cells in the culture plate. MTS/PMS solution (40 $\mu$l) was then added into each well maintaining a ratio of 40 $\mu$l MTS/PMS to 200 $\mu$l of medium. After 30 minutes the reduction product was measured at an absorbance of 490 nm and compared to a standardized curve.

EXAMPLE 11
Detection of Apoptosis

To determine the extent of apoptosis induced by the anti-erbB-2 sFv, cells were infected with adenovirus encoding the LacZ reporter gene, as a control, or the endoplasmic reticulum directed anti-erbB-2 sFv. At 48 hours post-infection, a cell suspension was prepared at $\sim 5 \times 10^5$ cells/ml in normal culture medium. The suspended cells (25 $\mu$l) were stained by the addition of 1 $\mu$l dye containing 100 $\mu$g/ml acridine orange and 100 $\mu$g/ml ethidium bromide. Cells were subsequently placed on a glass slide and examined by flourescent microscopy.

EXAMPLE 12
Quantification of breast cancer cell line erbB-2 levels

To determine levels of total erbB-2 protein produced by various breast carcinoma cell lines, total cellular protein was applied to a 96 well plate pre-coated with primary human erbB-2 antibody and assayed according to manufacturer's instructions using a quantitative HER2/neu (erbB-2) ELISA kit (Oncogene Science, Uniondale, N.Y.). Briefly, total cellular protein was isolated from cells in a cell lysis buffer solution containing 1×PBS (Phosphate Buffered Saline, pH 7.2), 1.5 mM EDTA (Ethylenediaminetetraacetic acid), 100 $\mu$M PMSF (Phenylmethanesulfonyl Fluoride) and 1 $\mu$g/mL aprotinin. Cell lysate was then plated at 1 $\mu$g protein/well, blocked and bound to the manufacturer's detector antibody. Using a peroxidase conjugate system, erbB-2 protein levels were determined by an absorbance reading at 490 nm. A standard curve was derived using the human neu unit (HNU) standards provided by the manufacturer. The test absorbances were compared to the standard curve and values were extrapolated using the Softmax Program (BioTek Instruments, Winooski, Vt.). The neu assay will detect 10 HNU (0.5 femtomoles erbB-2) per ml of cell lysate. The signal of 10 HNU is approximately twice the background signal. The human neu values obtained from the assay were then converted to femtomole erbB-2/$\mu$g protein.

EXAMPLE 13
Gene transfer to breast cancer cells

To determine the transduction efficiency of the employed vectors in the context of the breast cancer targets, an *E. coli* $\beta$-galactosidase (LacZ) reporter gene system was used. For this analysis, the human breast cancer cell lines were seeded into six-well tissue culture plates at a density of $3.33 \times 10^5$ cells per well. Twenty-four hours later, the cells were transduced with a recombinant adenovirus encoding the bacterial $\beta$-galactosidase gene, AdCMVLacZ, at 100 pfu/cell. At 48 hours post-infection, cells were assayed for $\beta$-galactosidase expression by flow cytometric methods using cells stained with flourescein-di-galactoside (FDG) (Sigma, St. Louis, Mo.). Briefly, cells were resuspended at a concentration of $1 \times 10^7$ cells/ml in staining meduim (PBS, pH 7.2 with 4% FCS and 10 mM HEPES). An aliquot of cells (100 $\mu$l) was incubated at 37° C. for 10 minutes, and stained with 100 $\mu$l pre-warmed 200 mM FDG for 1 minute. The reaction was quenched by addition of 1 ml of staining medium, and cells were immediately assayed for FDG uptake by Flourescence Activated Cell Sorter (FACS) analysis.

EXAMPLE 14
Down-regulation of cell surface erbB-2 by the anti-erbB-2 sFv.

Figure 10A:
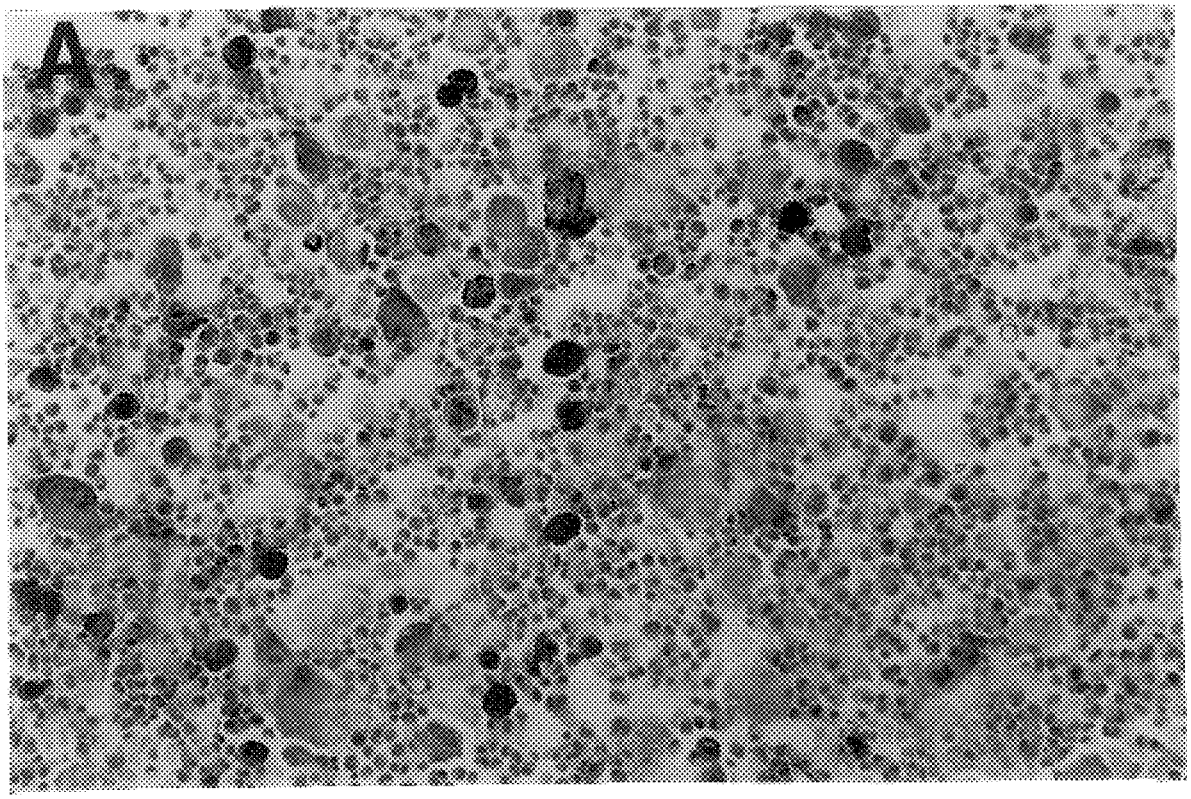
FIGS. 10A–10C show the down-regulation of cell surface erbB-2 in human breast cancer cells mediated by intracellular anti-erbB-2 single-chain antibody (sFv) delivery. The erbB-2 overexpressing human breast cancer cell line MDA-MB-361 was infected with either a LacZ reporter gene encoding adenovirus (AdCMVLacZ) or a recombinant adenovirus encoding an endoplasmic reticulum-directed anti-erbB-2 sFv. Post infection (24 hours) cells were evaluated for cell surface erbB-2 by immunohistochemistry with a polyclonal antitumor erbB-2 antibody and compared with uninfected control cells. A=Untransfected cells B=AdCMVLacZ transfected cells C=Ad21 transfected cells. Magnification=200×
Figure 10B:
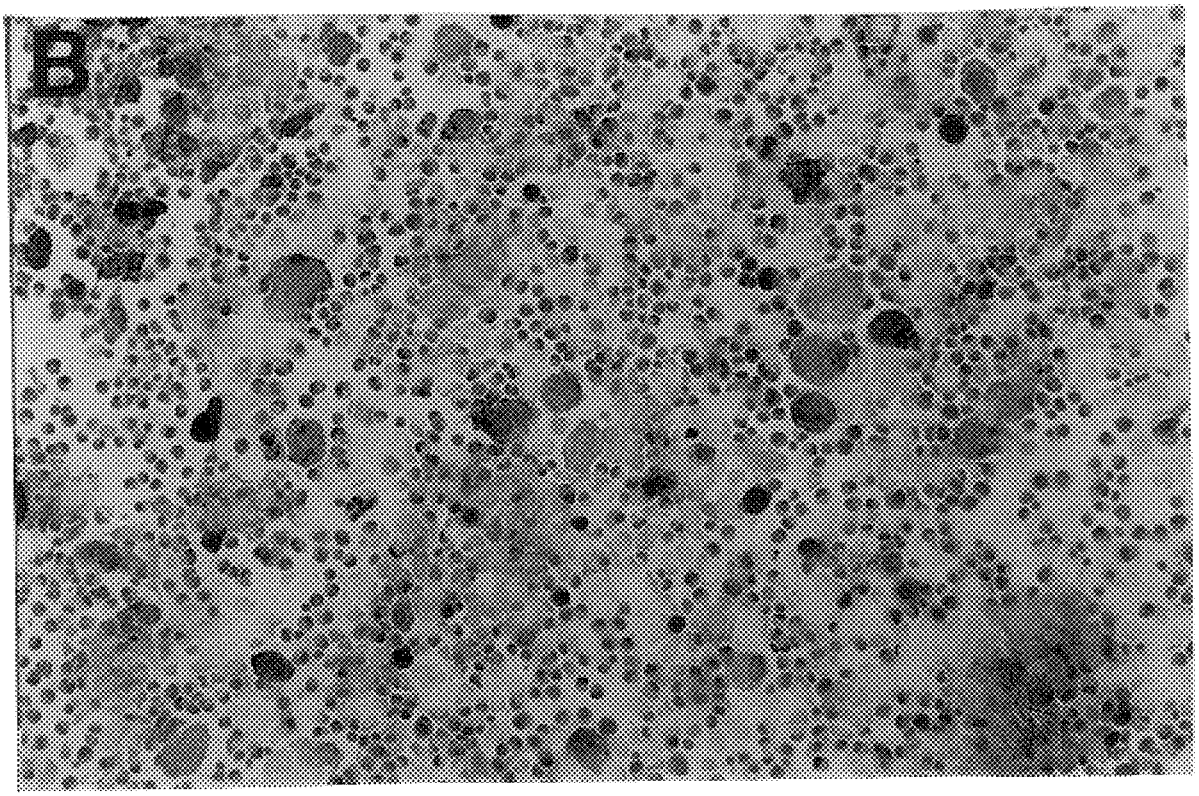
Figure 10C:
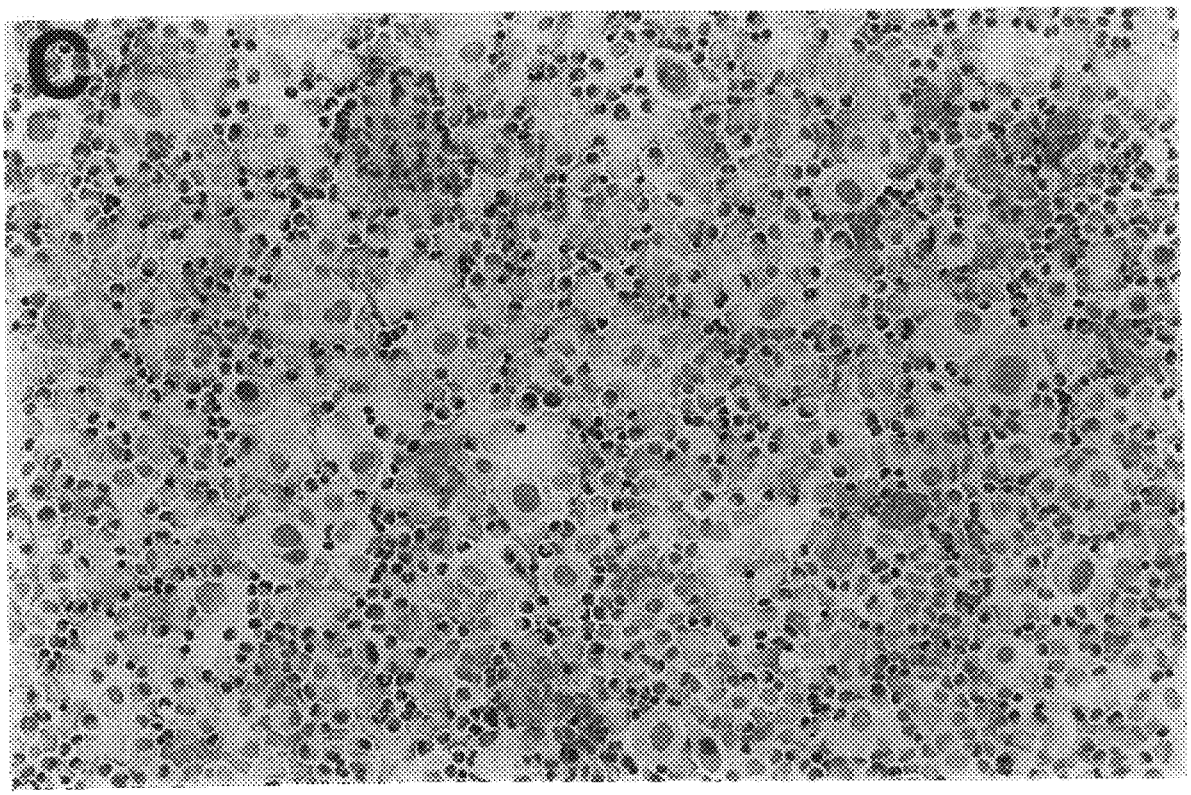

Intracellular expression of anti-erbB-2 sFv accomplishes down-regulation of cell surface erbB-2 in ovarian cancer cell lines. Furthermore, an endoplasmic reticulum directed form of the anti-erbB-2 sFv was uniquely capable of achieving this effect, presumably on the basis of entrapment of nascent erbB-2 in the endoplasmic reticulum of transduced tumor cells. The first cellular target was the erbB-2 overexpressing human breast carcinoma cell line MDA-MB-361. Gene transfer to these cells was accomplished by delivery of either a control adenovirus, AdCMVLacZ, or the endoplasmic reticulum directed anti-erbB-2 sFv, Ad21. Transduced cells were evaluated 24 hours after viral infection for cell surface erbB-2 expression by immunohistochemistry. In this analysis, the adenovirus encoding the endoplasmic reticulum directed anti-erbB-2 sFv resulted in a significant reduction in the amount of detectable cell surface erbB-2 (FIG. 10). In contrast, transduction with the control virus AdCMVLacZ did not result in any detectable down-regulation of cell surface erbB-2 levels when compared to untransfected cells. Thus, intracellular expression of the endoplasmic reticulum directed anti-erbB-2 sFv mediates down-regulation of cell surface erbB-2 in a human breast cancer cell line overexpressing erbB-2.

EXAMPLE 15
Specific cytotoxicity mediated by the anti-erbB-2 sFv in human breast cancer cells.

It was determined if the sFv-mediated erbB-2 down-regulation achieved in breast adenocarcinoma cells would induce specific tumor cell killing. A panel of human breast cancer cell lines was infected with either Ad21 or AdCMVLacZ recombinant adenovirus. A cell viability assay based upon the colormetric conversion of a tetrazolium salt to formazan by viable cells was carried out to determine cell viability at 96 hours post-infection.

Figure 11:
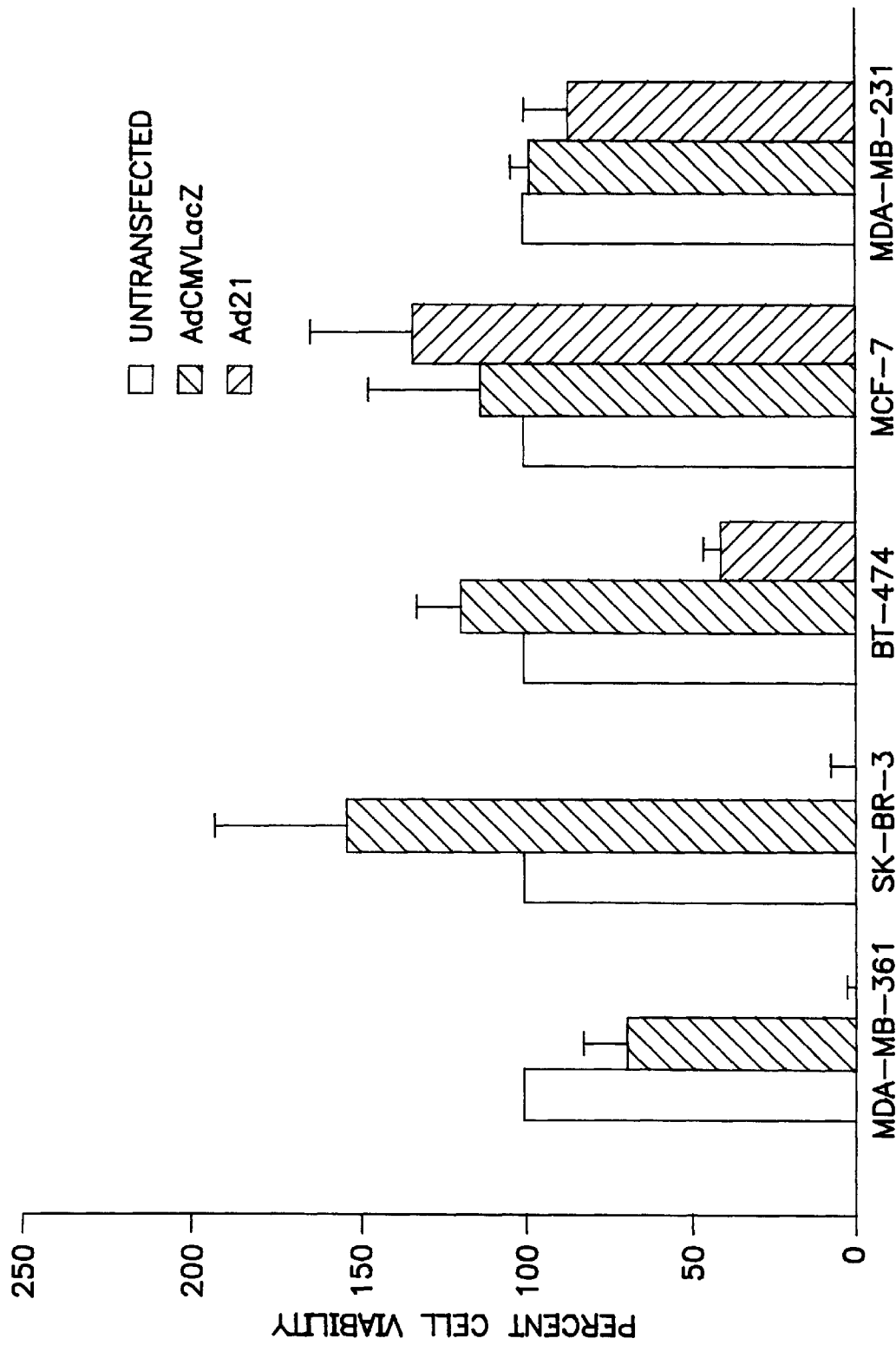
FIG. 11 shows the anti-erbB-2 sFv-mediated cytotoxicity in human breast cancer cell lines. The β-galactosidase encoding adenovirus, AdCMVLacZ, and Ad21, which encodes an endoplasmic reticulum-directed anti-erbB-2 sFv, were employed to evaluate cell viability by an MTA assay at 96 hours post-infection. Experiments were repeated three times. Results are reported as mean±SEM.

The various breast cancer cell lines differed appreciably with respect to sFv-mediated cytotoxicity (FIG. 11). None of the lines infected with the control virus AdCMVLacZ exhibited any cytotoxicity after infection. However, three of the breast cancer cell lines, SK-BR-3, MDA-MB-361 and BT-474, showed marked reduction in cell survival at 96 hours when infected with the anti-erbB-2 sFv encoding virus, Ad21. In contrast, the cell lines MCF-7 and MDA-MB-231 were relatively resistant to the cytotoxic effect of the sFv. This latter result could have reflected inadequate transduction frequency in these instances, and thus may not have revealed a true resistance to sFv-mediated anti-tumor effects. To exclude this possibility, transduction efficiencies were determined employing the reporter gene encoding adenovirus, AdCMVLacZ. Following viral infection, FACS analysis for β-galactosidase positive cells was undertaken. In this analysis, both cell lines exhibited a >95% transduction frequency (data not shown). Therefore, the differential cytotoxicity noted in this study appeared to reflect differences in breast cancer cell sensitivity to anti-erbB-2 mediated cytotoxicity and not differences in transducibility. Thus, while it could be shown that the anti-erbB-2 sFv caused cytotoxicity in human breast cancer cell lines, the effect was not uniform with respect to this tissue type.

EXAMPLE 16

Figure 12A:
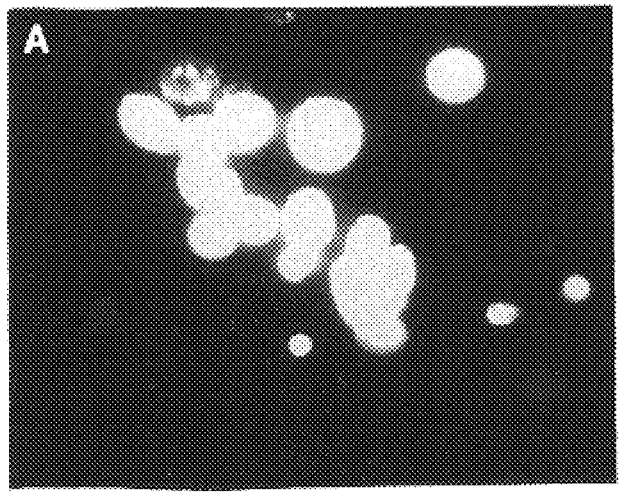
FIGS. 12A–12C show the induction of apoptosis in human breast cancer cell lines mediated by the anti-erbB-2 sFv encoding adenovirus Ad21. Forty-eight hours after transduction with either AdCMVLacZ or Ad21, SK-BR-3 cells were stained with a DNA-binding flourescent dye containing 100 μg/ml acridine orange and 100 μg/ml ethidium bromide to visualize cells undergoing apoptosis. A=Untransfected cells B=AdCMVLacZ transfected cells C=Ad21 transfected cells. Magnification=200×.
Figure 12B:
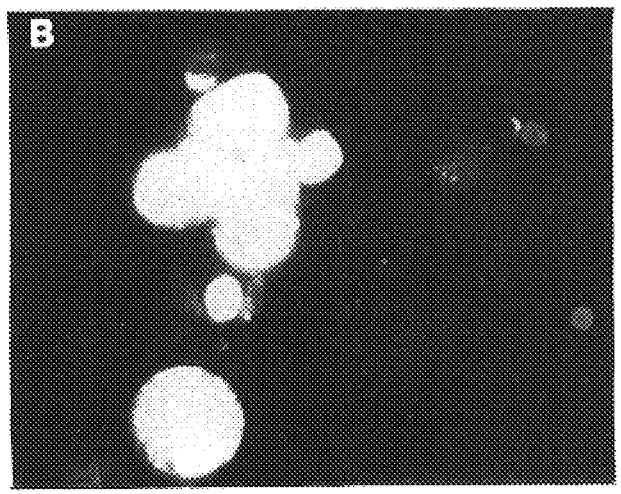
Figure 12C:
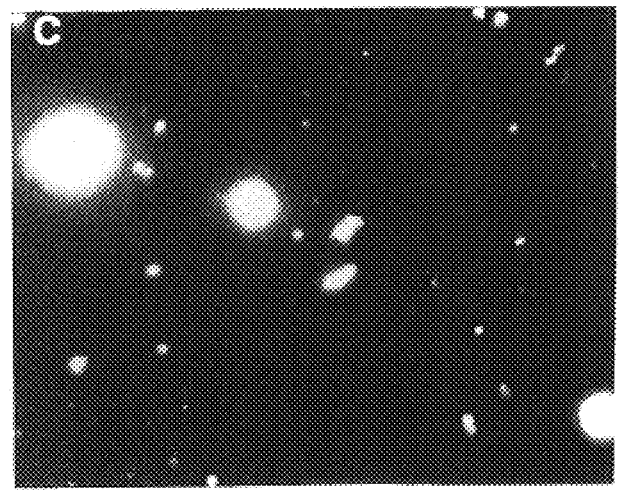

Anti-erbB-2 sFv mediated induction of apoptosis in erbB-2 overexpressing breast cancer cell lines Because delivery of the anti-erbB-2 sFv accomplished dramatic cytotoxicity in the breast cancer cell lines MDA-MB-361, SK-BR-3 and BT-474, whether the pathway of cell killing occurred via programmed cell death was investigated. Either control virus, AdCMVLacZ, or adenovirus encoding the endoplasmic reticulum directed anti-erbB -2 sFv, Ad21 was delivered, to one of the highly susceptible cell lines, SK-BR-3. The cells were subsequently stained with a flourescent DNA-binding dye that could differentiate between viable non-apoptotic, viable apoptotic, and non-viable apoptotic cells. The SK-BR-3 cells infected with AdCMVLacZ resembled those that were untransfected (FIG. 12). However, cells treated with the anti-erbB-2 sFv encoding adenovirus, Ad21, were apoptotic, as demonstrated by changes in visible color flourescence, vesicle formation, condensed chromatin, and characteristic apoptotic bodies. This observation confirms that sFv-mediated cytotoxicity in breast cancer cells occurs via the programmed cell death pathway.

EXAMPLE 17

Quantification of erbB-2 levels in breast cancer cell lines

Figure 13:
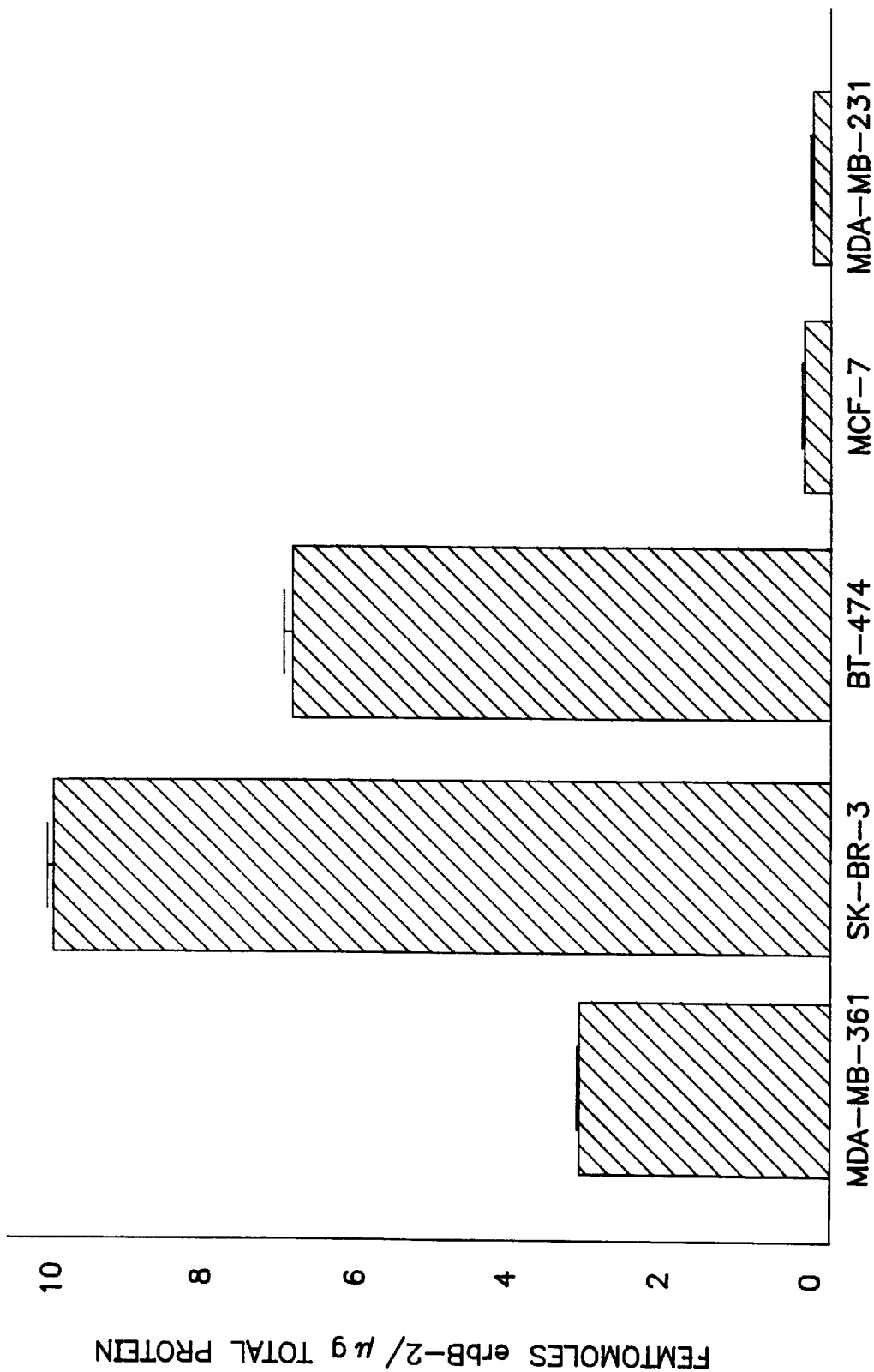
FIG. 13 shows the levels of erbB-2 protein in human breast cancer cell lines. A panel of human breast cancer cell lines were evaluated for cellular levels of the erbB-2 protein by ELISA. Relative erbB-2 levels were quantified against a standard curve. Determinants were repeated ×3 with results expressed as mean±SEM.

Whereas erbB-2 over-expression has been noted in up to 30% of human breast cancer cells, levels may be extremely variable in the remaining subset. Thus, the differences in anti-erbB-2 sFv sensitivity might reflect differences in the erbB-2 levels of target cells. To evaluate this, the levels of cellular erbB-2 in the tumor cell targets were determined by a sensitive ELISA assay. The breast cancer cells assayed differed appreciably with respect to cellular erbB-2 levels (FIG. 13). Significantly, a correlation was noted to exist between cellular erbB-2 levels and susceptibility to sFv-mediated cytotoxicity. Specifically, the cell lines which appeared resistant to the anti-erbB-2 sFv possessed the lowest levels of cellular erbB-2. In contrast, the cell lines which exhibited susceptibility to the anti-erbB-2 sFv overexpressed erbB-2. Thus, this analysis suggests that the endogenous level of cellular erbB-2 predicts tumor cell sensitivity to anti-erbB-2 sFv-mediated killing in the context of breast carcinoma.

The present invention demonstrated that intracellular expression of an anti-erbB-2 sFv both down-regulates cell surface erbB-2 and causes specific toxicity in erbB-2 overexpressing human breast cancer cells. Furthermore, the anti-erbB-2 sFv achieves cytotoxic results by inducing programmed cell death in the erbB-2 overexpressing cells. Tumor cell erbB-2 levels are predictive of their susceptibility to sFv-mediated cytotoxicity. The breast cancer cells lines overexpressing erbB-2, as determined by the erbB-2 ELISA, are killed by the sFv. In marked contrast, the non-erbB-2 overexpressing breast cancer cells are not adversely affected by the sFv in that there is no change in erbB-2 protein production or cell viability. The breast cancer cells evaluated did not represent a true range of erbB-2 levels which would permit precise dose-response relationships to be investigated. Nonetheless, there does appear to be a clear threshold effect whereby susceptibility could be predicted. Thus, a requisite level of both the sFv and its target may be required to trigger apoptosis.

The present invention offers a new gene therapy approach for carcinoma of the breast. Current breast cancer gene therapy strategies represent distinct methods to target disease at either the local-regional or disseminated stage. In the latter regard, genetic correction strategies are presently limited by the lack of vector systems capable of achieving tumor cell-specific delivery to widely dispersed neoplastic cells. Thus, approaches for disseminated disease have attempted to utilize genetic methods to achieve anti-tumor immunity.

The ability to accomplish a highly targeted tumor cell-specific cytotoxicity via the anti-erbB-2 sFv may have applications to various breast cancer gene therapy paradigms. The ability to accomplish targeted tumor cytotoxicity offers a high level of tumor specificity. Since sFv expression is non-toxic to cells not overexpressing erbB-2, this approach obviates the requirement to achieve tumor cell specific expression of the anti-cancer gene product. Based upon these findings, the utility of the anti-erbB-2 sFv approach for breast cancer carcinomatosis at serosal sites as a means to achieve a genetic debulking of disseminated tumor is possible.

EXAMPLE 18

Cell lines

The erbB-2 expressing human lung carcinoma cell lines A549, SKLU, H1299, H358 (provided by Jeff Kern, University of Iowa), the erbB-2 expressing human ovarian carcinoma cell line SKOV3 (ATCC, Rockville, Md.), the non-erbB-2 expressing human lung cancer line H520 and the human epithelial carcinoma cell line HeLa (ATCC), and the early passage 293 cell line (provided by F. Graham, McMaster University, Hamilton, Ontario, Canada) were maintained in complete media consisting of RPMI 1640 (A549, SKLU, H520, H1299, H358), DMEM (HeLa), or DMEM/F12 (SKOV3, 293) (Mediatech, Herndon, Va.) supplemented with L-glutamine (300 $\mu$g/ml), penicillin (100 i.u./ml), streptomycin (25 $\mu$g/ml), and 10% fetal calf serum (FCS) (PAA Laboratories, Newport Beach, Calif.) at 37° C. in a humidified 5% carbon dioxide atmosphere. For stable clones, G418 (GIBCO BRL, Gaithersburg, Md.) containing media was made as follows: After determining the G418 sensitivity of each cell line, the appropriate concentration of G418 was dissolved in 100 mM HEPES buffer, pH 7.3, and added to complete media. This was then filter sterilized using a 0.2 $\mu$M filter. For adenoviral transfections, 2% media was prepared exactly as above except for the addition of 2% FCS instead of 10%.

EXAMPLE 19

Generation of stable clones

Cells were transfected with plasmid DNA pGT21, a pcDNA3 derivative encoding the ER form of the anti-erbB-2 sFv, or pcDNA3 as a control construct, in 60 mm dishes with DOTAP (Boehringer-Mannheim, Indianapolis, Ind.)-plasmid DNA complexes according to the manufacturer's instructions. Briefly, 6.0 $\mu$g plasmid DNA in 50.0 $\mu$l HEPES was mixed with 30.0 $\mu$l DOTAP in 100 $\mu$l HEPES for 15 minutes. Complexed mixtures were added to 5 mL complete media and incubated with cells. After 24 hours, media was replaced with complete media. After transfection, cells were allowed to grow for 48 hours in non-selective media, at which point they were trypsinized and split 1:15 into five 60 mm dishes per cell line per transfected construct. These new dishes were grown in complete media containing between 0.25 mg/ml and 1.0 mg/ml G418 depending on the individual sensitivity of each cell line. Between 17 and 21 days, depending on the growth kinetics of individual cell lines, dishes of cells were fixed with buffered FormaldeFresh and stained with crystal violet. After overnight drying, colonies were counted. For each cell line, one dish of pcDNA3 and one dish of pGT21 transfected cells was used to isolate clones for further studies.

EXAMPLE 20
Generation of adenovirus-polylysine gene transfer vector

In order to accomplish gene transfer, two vector systems were employed. For the adenovirus-poly-L-lysine (AdpL) delivery method, plasmid DNAs were constructed encoding various forms of an anti-erbB-2 single chain immunoglobulin (sFv). Starting with the adenovirus dl1014, which contains a genomic deletion in the E4 region, AdpL conjugates were constructed via the EDC-linkage method. These complexes were then combined with the various plasmid DNAs to form adenovirus-poly-L-lysine-DNA complexes. For transient transfection experiments, the complexes were prepared as described. Briefly, conjugate-DNA complexes were formed by the sequential addition of 100 $\mu$l of AdpL conjugate, 6.0 $\mu$g plasmid DNA diluted in 200 $\mu$l of 150 mM NaCl, 20 mM HEPES, pH 7.3 (HBS) and 4.0 $\mu$g poly-L-lysine (Sigma, St. Louis, Mo.) diluted in 200 $\mu$l HBS. A volume of formed complex was then added to 2% media and added to the cells. After one hour, complete (10%) media was then added to the cells. Plasmids employed included the control plasmid pcDNA3 (Invitrogen, San Diego, Calif.), as well as pcDNA3 modified to encode a cytosolic form of the anti-erbB-2 sFv (pGT20) or an endoplasmic reticulum (ER) form of the anti-erbB-2 sFv (pGT21).

EXAMPLE 21
Generation of recombinant adenoviruses

Recombinant adenoviruses expressing the anti-erbB-2 sFvs were prepared employing standard homologous recombination techniques. Briefly, DNA fragments containing the anti-erbB-2 sFv genes were cut from their parent plasmids using the restriction enzymes Kpn I and Xba I (New England Biolabs, Beverly, Mass.) and then ligated into the polylinker region of the adenoviral shuttle vector pACCMVpLpARS (+) (provided by R. Gerard, University of Texas-Southwestern, Dallas, Tex.). This plasmid provides promoter/initiation signals derived from the CMV early promoter/enhancer and polyadenylation signals from SV40. The resulting recombinant adenoviral shuttle plasmids pAC20 and pAC21 were then employed to derive the E1-deleted, replication-defective, recombinant adenoviruses employing standard methodologies (Becker, T C, et al., *Methods Cell Biol.* 1994 43: p. 161–89). Briefly, the shuttle plasmid and the adenoviral packaging plasmid pJM17 (provided by F. Graham) were co-transfected into the E1A trans complementing cell line 293 employing the commercial cationic liposome vector DOTAP. Transfected cells were maintained until the onset of cellular cytopathic effects. The newly generated recombinant adenoviruses were plaque purified three times. Validation of single plaques was accomplished by direct polymerase chain reaction (PCR). The recombinant adenoviruses encoding the anti-erbB-2 sFv genes, Ad20 and Ad21, were expanded within 293 cells and purified by CsCl gradient centrifugation. Adenoviral vectors were titered within the cell line 293, employing plaque assay techniques for direct determination of viral plaque forming units (PFU). The recombinant adenovirus AdCMVLacZ (provided by D. Tang, Univ. of Alabama, Birmingham, Ala.), expressing the $\beta$-galactosidase gene, has been described (Tang, D., et al., *Cancer Gene Ther.* 1994; 1(1) 15–20).

EXAMPLE 22
Determination of cytotoxicity

The effect of expression of the anti-erbB-2 sFv on cell growth kinetics and viability was determined employing the CellTiter 96 AQueous Non-Radioactive Cell Proliferation/ Cytotoxicity Assay (Promega, Madison, Wis.) which is an MTS colorimetric test for the ability of viable cells to convert a tetrazolium salt to a formazan compound. To accomplish this analysis, monolayers of cells were seeded into 96 well cell culture plates at a density of 5000 cells per well. Two separate methods were employed to transfer the sFv gene constructs to target cells. The first method employed the Adenovirus-polylysine (AdpL) vector system for transient transfection of the target cells with pcDNA3, pGT20 or pGT21. A 2.5 $\mu$l portion of a single AdpL complex was mixed with 100 $\mu$l of appropriate 2% media and incubated with the cells for 1 hour, at which point 100 $\mu$l complete media was added. The plates were subsequently incubated for 5 days post-transfection. The second method employed the various recombinant adenoviruses. Infection of target cells employed standard methods. Briefly, cells were seeded into 96 well plates as described above, and infection was done at a multiplicity of infection (MOI) of 100 PFU per cell in 2% media. After an hour, complete (10%) media was added. At 5 days post transfection, the CellTiter 96 kit was used according to the manufacturer's instructions. Percent viability was calculated by the formula: [(infected cells−blank)/uninfected cells−blank)]×100.

EXAMPLE 23
Effects of anti-erbB-2 sFv expression on the derivation of stable clones in erbB-2 positive and negative human lung cancer cell lines To evaluate the toxicity of anti-erbB-2 sFv independent of transfection efficiency, stable clones were derived from several human lung cancer cell lines. A differential in stable clone derivation is a common assay used to indicate cytotoxicity due to expression of particular genetic constructs. These experiments have the added advantage of correcting for transfection efficiency, which can complicate interpretation of results using transient expression systems. The plasmid pGT21, encoding the ER form of the sFv, and the control plasmid pcDNA3 were used in these experiments. As shown in TABLE 3, all erbB-2 positive cell lines showed a significant differential in stable clone derivation with decreased clones noted with pGT21 transfection. In addition, a small number of clones were analyzed for sFv expression using a western blot. These analyses showed that 0/6 clones tested expressed the sFv (data not shown). Together, these results indicate that expression of the erbB-2 sFv construct significantly reduces the number of viable stable clones. Of note, the lung cancer cell line H520, which does not express erbB-2, showed no difference in the number of stable clones derived from either construct. These results indicate that the expression of the anti-erbB-2 sFv in erbB-2 positive lung cancer cell lines is relatively incompatible with outgrowth of tumor clones. Also, erbB-2 status is correlated with sensitivity to the sFv.

TABLE 3

Effect of anti-erbB-2 sFv on derivation of stable clones

| Cell Line | erbB2 | G418 Resistant Colonies Level[1] | |
|---|---|---|---|
| | | pcDNA3 | pGT21 |
| NCI-H520 | 0 | 27 ± 5.0 | 22.4 ± 4.1 |
| H1299 | 13 | 4 ± 1.6 | 1 ± 0.82 |
| H358 | 15 | 17.25 ± 5 | 5 ± 1.2 |
| SKLU | 27 | 10 ± 4.2 | 0.25 ± 0.5 |

Table 3: Cell lines were transfected with either the pcDNA3 or pGT21 construct using DOTAP. At 48 hours, G418 was added to the media. At 21 days post-transfection, colony numbers were evaluated. Results are from 5 separate experiments and are expressed as mean ± SEM.

EXAMPLE 24

Targeted cytotoxicity by anti-erbB-2 sFv in A549 lung carcinoma cells

Figure 14:
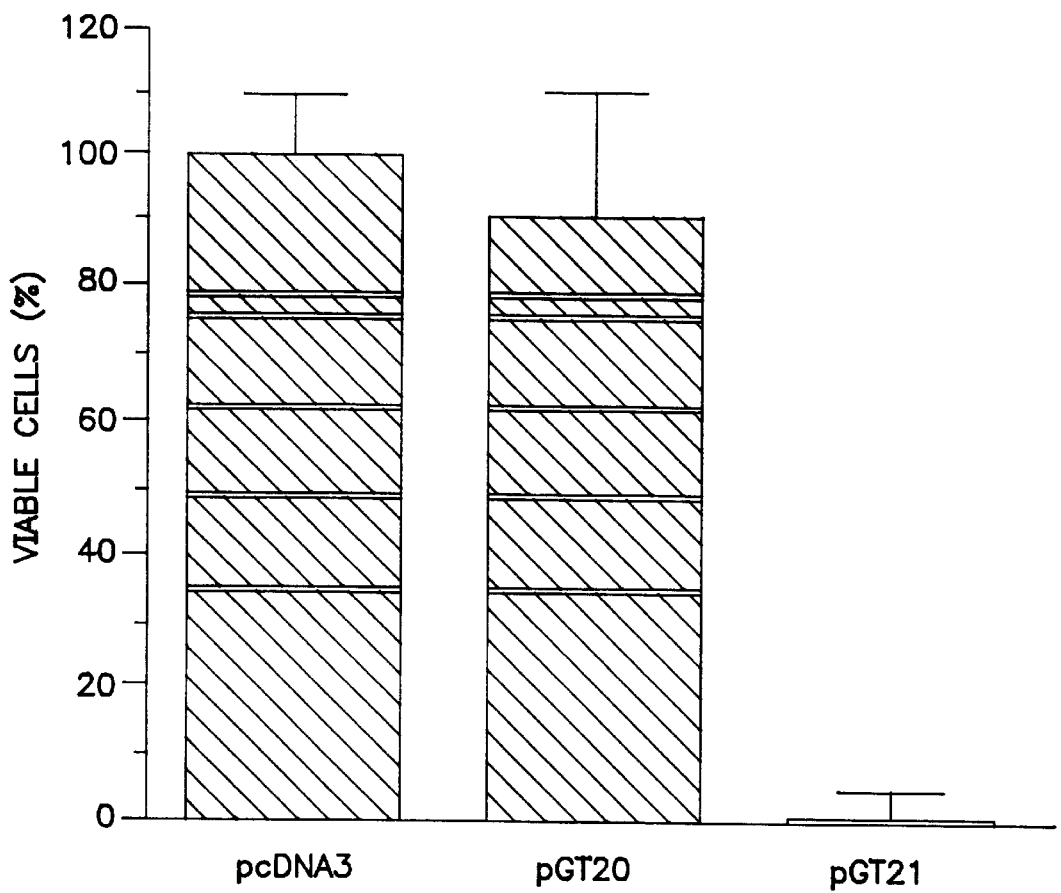
FIG. 14 shows the effect of the anti-erbB-2 sFv on cell viability in the cell line A549. A549 cells were transfected via the AdpL system with either the pcDNA3, pGT20, or pGT21 construct and evaluated at 5 days post-transfection using an MTS assay of cell viability. Percent cell viability is expressed as a percentage of cells transfected with pcDNA3 control plasmid DNA. Results from 6 experiments are expressed as mean+/−SEM.

The AdpL system employs a replication-incompetent adenovirus complexed with poly-L-lysine to transiently transfect cells of many tissue types. After verifying high level transfection of the lung cancer cell line A549 with this vector system, the effects of the anti-erbB-2 sFv on cell viability were analyzed. To accomplish this analysis, the MTS assay was utilized as a measure of cell viability. The A549 cells were transfected with either pcDNA3, pGT20, or pGT21, and then analyzed five days post-transfection for viable cell number (FIG. 14). SKOV3 and HeLa cells were used as positive and negative controls, respectively (data not shown). Also, the lung cancer cell line NCI-H520 (erbB-2 negative) was employed as an additional control. In the case of A549 cells and the SKOV3 control, there was an observed decrease in the number of viable cells such that greater than 95% of tumor cells had been killed at 5 days post-transfection. This cytotoxic effect was noted only in the context of the ER targeted anti-erbB-2 sFv construct pGT21. In marked contrast, neither HeLa nor NCI-H520 cells showed significant differences in viable cell number when transfected with the vector control and either of the sFv constructs. Thus the anti-erbB-2 sFv induces selective cytotoxicity in erbB-2 expressing A549 lung cancer cells.

EXAMPLE 25

Figure 15:
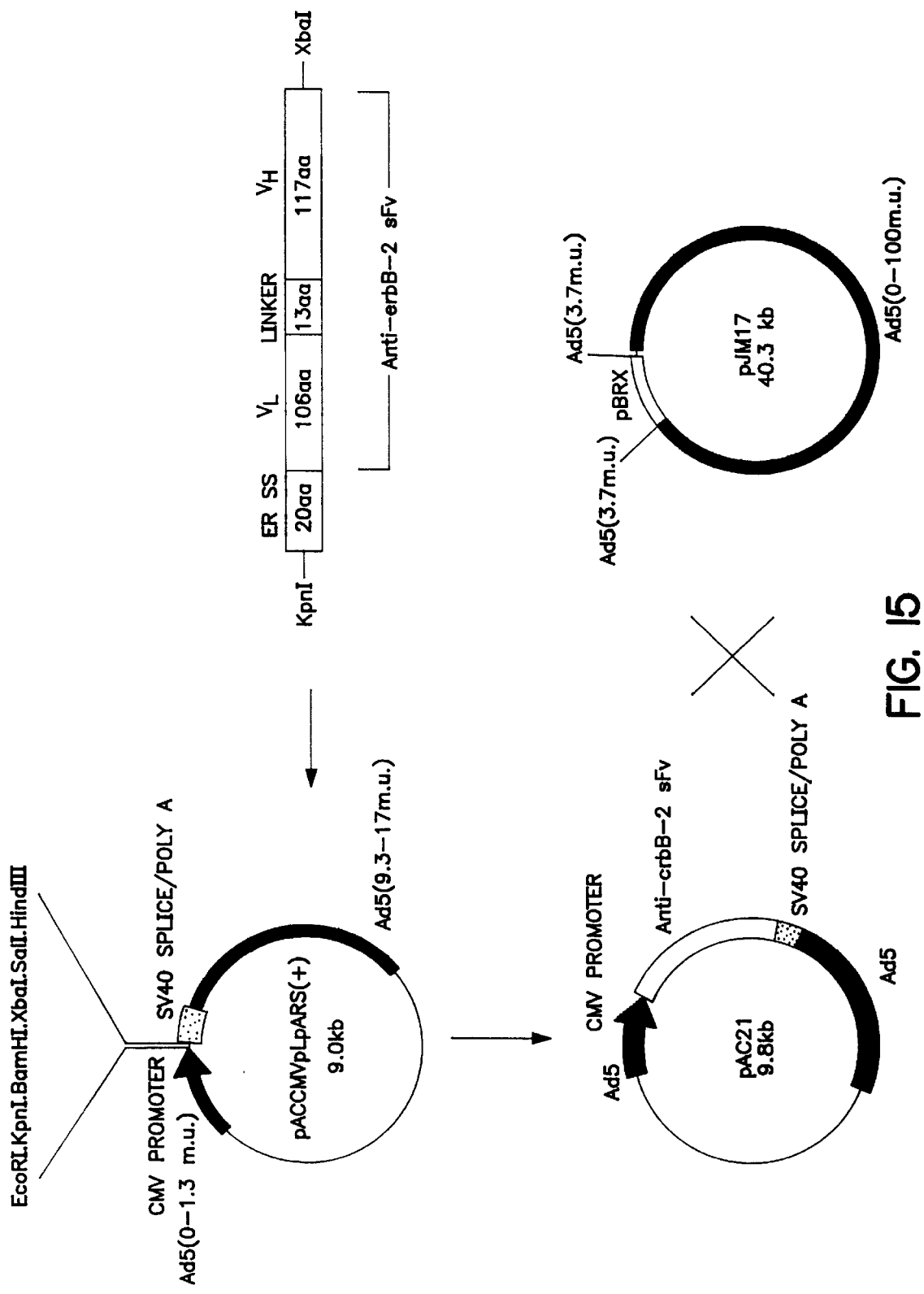
FIG. 15 shows a schema for construction of recombinant adenovirus expressing the anti-erbB-2 sFv constructs. The adenoviruses Ad20, encoding the cytosolic form of the anti-erbB-2 sFv, and Ad21, encoding the ER localized form of the anti-erbB-2 sFv, were constructed by identical methodologies. The construction of Ad21 is representative and was as follows. Depicted is a schema for the strategy employed to construct sFv encoding adenoviruses. Restriction digestion of the original anti-erbB-2 sFv expressing plasmids liberated a 0.77 kb fragment containing the sFv. This fragment was ligated into the shuttle vector backbone pACCMVpLpARS(+), which contains a portion of the Ad5 genome with a CMV promoter, a polylinker, and an SV40 splice site and poly A tail. The resulting shuttle vector was cotransfected into 293 cells along with the packaging plasmid pJM17. After observing cytopathic effect, the recombinant adenovirus was plaque purified three times. (ER SS=Endoplasmic Reticulum Signal Sequence; $V_L$=Variable Light Chain; Linker=Peptide Linker; $V_H$=Variable Heavy Chain).
Figure 16:
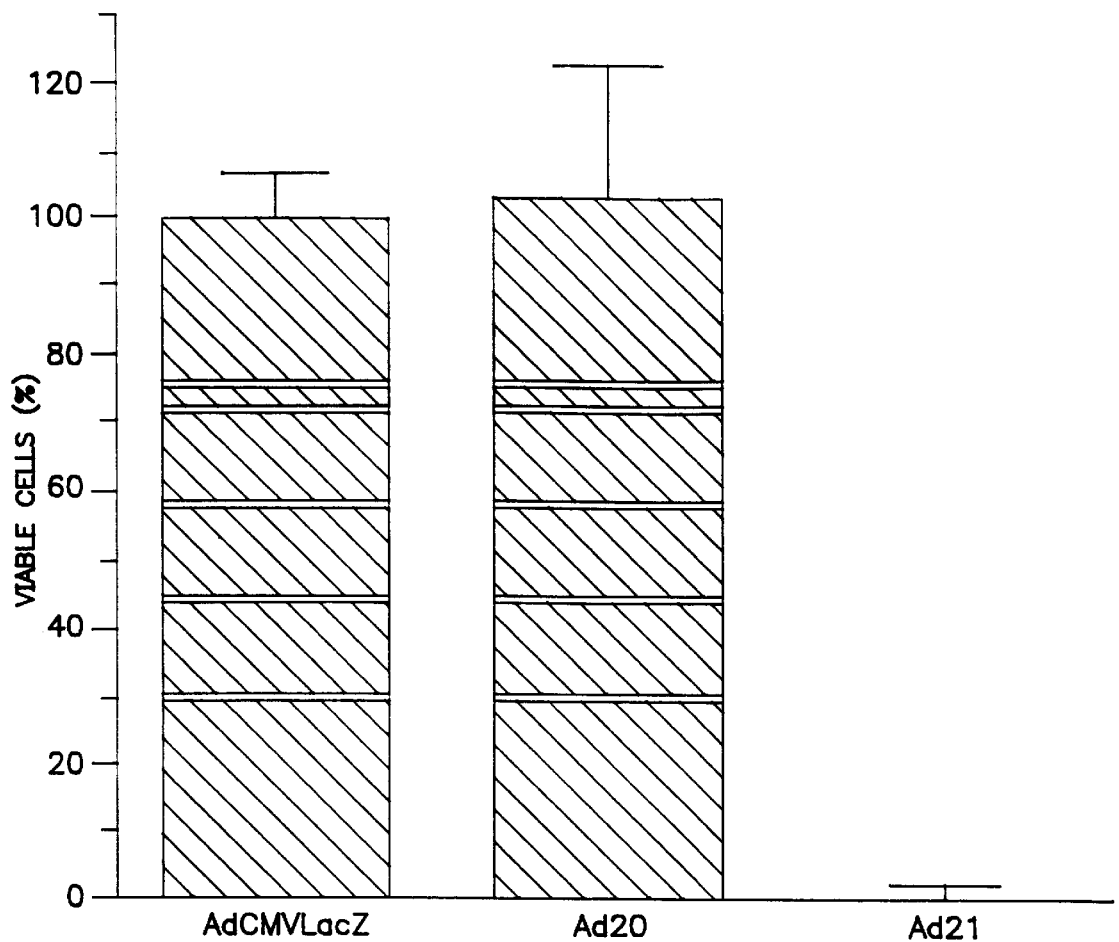
FIG. 16 shows efficacy of recombinant adenoviruses encoding the anti-erbB-2 sFv constructs in accomplishing specific cytotoxicity in the lung cancer cell line A549. The recombinant adenoviral vectors Ad20 and Ad21 were used to infect A549 cells at an MOI of 100 particles per cell. AdCMVlacZ, an adenovirus expressing β-galactosidase, was employed as a control transfection. Cells were evaluated at a single 5 day time point using the MTA assay. Percent cell viability is expressed as a percentage of cells transfected with AdCMVlacZ control adenovirus. Results from 6 experiments are expressed as mean+/−SEM.

Construction of recombinant adenoviruses expressing the anti-erbB-2 sFv constructs The above results with stable clones suggest that erbB-2 knockout with an intracellular sFv appears to have efficacy in the context of lung cancer. As a next step, these findings were translated into a practical approach to accomplish lung cancer gene therapy. The anti-erbB-2 sFv was configured into a replication deficient adenoviral vector, as this vector has proven utility in the context of direct in vivo gene transfer to human lung cancer cells. This construction employed standard methods and is shown in FIG. 15. The schema depicted demonstrates the construction of the adenovirus expressing the ER targeted form of the anti-erbB-2 sFv known as Ad21. An identical technique was utilized to construct the adenovirus expressing the cytosolic form of the anti-erbB-2 sFv, Ad20. This methodology for recombinant adenovirus construction is based upon in vivo homologous recombination between the recombinant adenoviral shuttle vector and the adenoviral packaging plasmid pJM17. In this strategy, recombinants allowing replacement of the wild-type left terminus of the adenovirus genome, with excision of the heterologous pBRX segments, may possess packaging advantages compared to the oversized pJM17 adenoviral genome-containing plasmid. The adenoviral shuttle vector containing the ER targeted anti-erbB-2 sFv, pAC21, was thus constructed and employed to derive the corresponding adenoviral vector. The resulting adenoviral vector would be predicted to contain the sFv expression cassette inserted in place of deleted adenoviral E1 sequences (FIG. 16A). Based upon this genomic deletion, the resultant vector would be replication-defective in non-E1A transcomplementing cells.

Co-transfection of the adenoviral shuttle vector pAC21 and the packaging plasmid pJM17 in the E1A transcomplementing cell line 293 resulted in the demonstration of multiple areas of cytopathic effect consistent with adenoviral replication. Analysis of the viral DNA by PCR demonstrated the presence of recombinant adenovirus possessing characteristics consistent with the sFv vector predicted in FIG. 15, including E1A deletion, which confirms that recombinant adenovirus was replication-deficient. Similar structural analyses were performed with Ad20 (data not shown). These studies thus confirm that recombinant adenoviruses containing anti-erbB-2 sFv expression cassettes that are capable of achieving expression of the anti-erbB-2 sFv constructs have been derived.

EXAMPLE 26

Effects of anti-erbB-2 expressing recombinant adenovirus on human lung cancer cell viability To verify that the anti-erbB-2 sFv functioned in the context of a recombinant adenoviral delivery system, an assay of cell viability identical to that used for the AdpL transfections was employed. First, evaluation of efficiency of transduction was performed using the recombinant adenovirus AdCMVLacZ, which expresses the β-galactosidase gene. These studies verified that A549 cells could be transduced at greater than 95% efficiency when transfected at an MOI of 100 PFU per cell (data not shown). To demonstrate the utility of the recombinant adenoviral constructs, standard methods were employed. Cells were transfected at an MOI of 100 particles per cell, then evaluated at 5 days for viability via the MTS assay described above (FIG. 16). Cytotoxicity was only evident in those cells treated with Ad21, the adenovirus encoding the ER targeted anti-erbB-2 sFv. Those cells transfected with Ad20, which expresses a cytosolic form of the sFv, showed no significant difference in viable cell number when compared to cells transfected with the control virus AdCMVLacZ. As before, both HeLa and NCI-H520 cells were used as erbB-2 negative controls, and both showed no significant toxicity when treated with Ad21 (data not shown). Thus, the present invention conclusively shows that the ER targeted form of the anti-erbB-2 sFv is specifically cytotoxic to those cells which express erbB-2. This effect is seen regardless of the gene transfer vector used. An anti-erbB-2 sFv expressing vector system should prove useful for in vivo treatment models has been developed.

Most humans have been exposed to adenovirus naturally and thus a high proportion of the patient population may demonstrate some degree of immunity to these vectors. Whether this natural immunity will interfere with treatment is still uncertain. Another potential problem with adenoviral vectors is their high degree of tropism for most human cells. Thus, ectopic transduction mediated by the adenovirus could potentially alter erbB-2 sFv expression in non-tumor tissue. Although erbB-2 is expressed at low levels in most normal tissues, the possibility exists that nonspecific toxicity could occur in these cells. Studies utilizing a peritoneal model of ovarian cancer have been negative for nonspecific effects. Because of the compartmental nature of lung cancer, effective vector containment should be achievable, thus further reducing nonspecific cytotoxicity. Finally, the transduction efficiency of adenovirus, while better than most other vectors, is still less than 100%. Because of the importance of eliminating all tumor cells in the patient, multiple treatments may be necessary. However, the requirement for complete transduction may not be absolute. Apoptotic cells may serve to stimulate immune recognition of established tumor cells, thus making this approach much more effective.

EXAMPLE 27
Intracellular antibody mediated down-regulation of $p185^{erbB2}$ expression in malignant prostatic cells Metastatic prostatic adenocarcinoma demonstrates little response to conventional therapies. A novel technique to down-regulate the membrane expression of $p185^{erbB2}$ in the malignant prostatic cell lines DU145, LnCaP and PC3 was used. The cell lines were transfected with an adenovirus-polylysine (adpL) vector system with gene constructs encoding an anti-$p185^{erbB2}$ single chain (sFv) antibody. The plasmid pGT21 encodes a sFv with a signal sequence which reatins $p185^{erbB2}$ in the endoplasmic reticulum and prevents transit to the membrane. The number of viable cells was determined using a tetrazolium conversion assay at 72 hours post-transfection. Using the AdpL vector system, all cell lines demonstrated transfection efficiencies of >90%. Transfection with the anti-$p185^{erbB2}$ sFv resulted in an 80–90% decrease in viable cell number in the DU145 and LNCaP cell lines but had no significant effect on the PC3 cell line. Western blot analysis demonstrated significantly less $p185^{erbB2}$ expression in the PC3 cell line as comared to the DU145 or LNCaP cell line. Thus, an association between $p185^{erbB2}$ expression and sensitivity to $p185^{erbB2}$ down-regulation was observed.

Any patents or publications mentioned in this specification are indicative of the levels of those skilled in the art to which the invention pertains. These patents and publications are herein incorporated by reference to the same extent as if each individual publication was individually incorporated by reference.

One skilled in the art will readily appreciate that the present invention is well adapted to carry out the objects and obtain the ends and advantages mentioned, as well as those inherent therein. The present examples along with the methods, procedures, treatments and specific compounds described herein presently representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A method for killing a neoplastic cell expressing an oncoprotein that stimulates proliferation of the cell, comprising introducing into the cell a nucleic acid molecule encoding an antibody homologue, wherein said oncoprotein is erbB2, wherein the antibody homologue is expressed intracellularly and binds to the protein intracellularly, to thereby kill the cell.

2. The method of claim 1, wherein the oncoprotein is normally expressed in mature form on the cell surface and the antibody homologue binds to the oncoprotein intracellularly in the endoplasmic reticulum of the cell.

3. The method of claim 2, wherein the antibody homologue is selected from the group consisting of a single chain Fv fragment and a Fab fragment.

4. The method of claim 1, wherein nucleic acid molecule is a recombinant expression vector selected from the group consisting of a viral vector and a plasmid vector.

5. The method of claim 1, wherein said neoplastic cell is from a tissue or organ selected from the group consisting of breast, gastrointestinal tract, lung and salivary gland.

6. A method for inhibiting survival of erbB2-overexpressing tumor cells in a mammal, comprising introducing into the tumor cells a nucleic acid molecule encoding an antibody homologue, wherein the antibody homologue is expressed intracellularly and binds to erbB2 intracellularly in the endoplasmic reticulum of the tumor cells, to thereby inhibit survival of the tumor cells.

7. The method of claim 6, wherein the antibody homologue is a single chain Fv fragment.

8. The method of claim 6, wherein nucleic acid molecule is a recombinant expression vector selected from the group consisting of a viral vector and a plasmid vector.

9. The method of claim 6, wherein the tumor cells are epithelial carcinoma cell from a tissue or organ selected from the group consisting of breast, gastrointestinal tract, lung and salivary gland.

* * * * *